US012799134B2

(12) United States Patent
Yu et al.

(10) Patent No.: US 12,799,134 B2
(45) Date of Patent: Nov. 17, 2026

(54) N-MACROCYCLIC AMIDE COMPOUNDS, PREPARATION METHODS THEREOF AND APPLICATIONS THEREOF AS MEDICAMENTS

(71) Applicant: Chengdu FANXI Biopharma Co., Ltd., Chengdu (CN)

(72) Inventors: Niefang Yu, Chengdu (CN); Hao Li, Chengdu (CN); Xin Chen, Chengdu (CN); Xiaoyu Liu, Chengdu (CN)

(73) Assignee: Chengdu FANXI Biopharma Co., Ltd., Chengdu (CN)

( * ) Notice: Subject to any disclaimer, the term of this patent is extended or adjusted under 35 U.S.C. 154(b) by 540 days.

(21) Appl. No.: 18/337,337

(22) Filed: Jun. 19, 2023

(65) Prior Publication Data

US 2024/0425518 A1 Dec. 26, 2024

(51) Int. Cl.
*C07D 498/08* (2006.01)

(52) U.S. Cl.
CPC .................................. *C07D 498/08* (2013.01)

(58) Field of Classification Search
CPC .................................................... C07D 498/08
See application file for complete search history.

(56) References Cited

U.S. PATENT DOCUMENTS 3,134,672 A * 5/1964 Blout ....................... G03C 8/18 430/467
2017/0022202 A1 1/2017 Diels et al.

FOREIGN PATENT DOCUMENTS

CN 101365703 A1 2/2009
WO 2007/058628 A1 5/2007
WO 2013/139697 A1 9/2013

OTHER PUBLICATIONS

William et al., J. Med. Chem. 2011, 54, 13, 4638-4658.*
Kamil A. Lipinski, Louise J. Barber, Matthew N. Davies, Matthew Ashenden, Andrea Sottoriva, Marco Gerlinger, Cancer Evolution and the Limits of Predictability in Precision Cancer Medicine. Trends in Cancer, 2016, 49-63. (Year: 2016).*

* cited by examiner

*Primary Examiner* — Rebecca L Anderson
(74) *Attorney, Agent, or Firm* — Calfee, Halter & Griswold LLP

(57) ABSTRACT

The present invention relates to N-macrocyclic amide compounds with structures shown in a general structural formula (I) and a general structural formula (II) or isomers, diastereomers, enantiomers, prodrugs and pharmaceutically acceptable salts of the N-macrocyclic amide compounds, wherein L, X, Y, Z, $R^1$, A, B and C are respectively defined in the specification. The invention further relates to application of the N-macrocyclic amide compounds with the structure shown in the general structural formula (I) and the general structural formula (II) or isomers, diastereomers, enantiomers, prodrugs and pharmaceutically acceptable salts of the N-macrocyclic amide compounds as a medicament.

General structural formula (I)

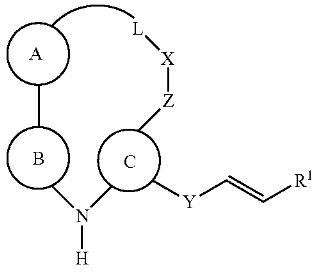

General structural formula (II)

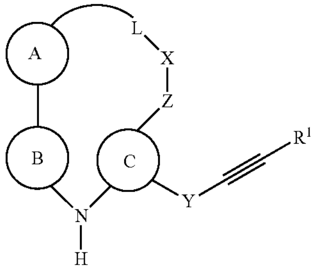

11 Claims, No Drawings

N-MACROCYCLIC AMIDE COMPOUNDS, PREPARATION METHODS THEREOF AND APPLICATIONS THEREOF AS MEDICAMENTS

TECHNICAL FIELD

The present invention relates to the field of pharmaceuticals, and particularly relates to N-macrocyclic amide compounds, preparation methods thereof and applications thereof as medicaments.

BACKGROUND

Human proliferative diseases usually involve the abnormal control of in-vivo cell growth and/or division, leading to the uncontrolled growth of in-vivo cells, and the formation and ultimate death of tumors (Jessica L. Counihan, Elizabeth A. Grossman, and Daniel K. Nomura. Cancer Metabolism: Current Understanding and Therapies. Chem. Rev. 2018, 118, 6893-6923).

With the improvement of human living standards, higher requirements are proposed for the clinical treatment of cancers. On one hand, it is necessary to further improve the curative effect needs, and on the other hand, it is also necessary to continuously reduce the related side effects and improve the living quality after prognosis. Targeted tumor therapeutic drugs emerge at the right moment. In numerous targeted anti-tumor drugs, a protein kinase ("kinase") inhibitor used as an anti-tumor drug has achieved great success and become an important class of the targeted anti-tumor drugs (Kinase inhibitors: the road ahead. Fleur M. Ferguson, and Nathanael S. Gray. Nature Review Drug Discovery, 2018. Volume 17, 353-377).

The growth, division and apoptosis of cells are controlled by signaling cascade or cell-signaling pathway. Kinase-mediated protein phosphorylation plays an important role in the above signal transduction. Studies found that the occurrence and growth of cancers are closely related to cell signal transduction, cell cycle regulation, cell apoptosis induction and tumor vessel growth. The kinase is mainly responsible for the control of intracellular signal transduction. The abnormal expression of the kinase is closely related to the occurrence and development of many diseases, especially tumors (Evolution of Small Molecule Kinase Drugs. Helen Louise Lightfoot, Frederick Woolf Goldberg, and Joerg Sedelmeier. ACS Med. Chem. Lett. 2019, 10, 153-160. Kinase Inhibitors for the Treatment of Immunological Disorders: Recent Advances. Marian C. Bryan and Naomi S. Rajapaksa. J. Med. Chem. 2018, 61, 9030-9058).

Janus kinases (JAK), comprising JAK1, JAK2, JAK3 and TYK2, belong to cytoplasmic protein kinases, react with type-I and type-II cytokine receptors, and regulate cytokine signal transduction (Advantages of targeting the tumor immune microenvironment over blocking immune checkpoint in cancer immunotherapy. Signal Transduction and Targeted Therapy (2021) 6:72-85). Downstream substrates of the JAK family comprise signal transducers and activators (STAT) of transcription proteins. JAK/STAT signal transduction involves many abnormal immune reactions, such as allergy, asthma and autoimmune diseases, comprising transplant rejection, rheumatoid arthritis, muscle contraction lateral sclerosis and multiple sclerosis, and solid and blood malignant tumors such as leukemia and lymphoma (Kinase Inhibitors for the Treatment of Immunological Disorders: Recent Advances. Marian C. Bryan and Naomi S. Rajapaksa. J. Med. Chem. 2018, 61, 9030-9058).

Compounds regulating the JAK kinases and combinations containing these compounds seem to provide substantial therapeutic effects for various patients. Therefore, it is urgent to develop inhibitors used for more related protein kinases, and specifically, it is urgent to develop more JAK family kinase inhibitors (Christoph Rummelt, Sivahari P. Gorantla, Manja Meggendorfer, Anne Charlet, Cornelia Endres, Konstanze Döhner, Florian H. Heidel, Thomas Fischer, Torsten Haferlach, Justus Duyster, Nikolas von Bubnoff. Activating JAK-mutations confer resistance to FLT3 kinase inhibitors in FLT3-ITD positive AML in vitro and in vivo. Leukemia, 2020:1-13. https://doi.org/10.1038/s41375-020-01077-1).

A novel macrocyclic structure may be used as an important structural unit of the kinase inhibitor. US20170022202A1 reported a synthesis method of Compound_1 and an analogue thereof and an application thereof as a kinase inhibitor. Compound_2 of Central South University is a kinase and a HDAC inhibitor, with potential medical applications (CN101365703A; and WO2007058628A1). Incyte Company reported a large number of macrocyclic compounds (WO2009132202A2) with various kinase inhibitory activities, with a representative compound shown in Compound_3. Polyphor Company takes the synthesis of a macrocyclic compound as an important platform to synthesize and screen various types of compounds in sequence, and Compound_4 is one of representative compounds. The macrocyclic compound of Polyphor Company has various potential medical applications (WO2013139697A1).

Compound_1

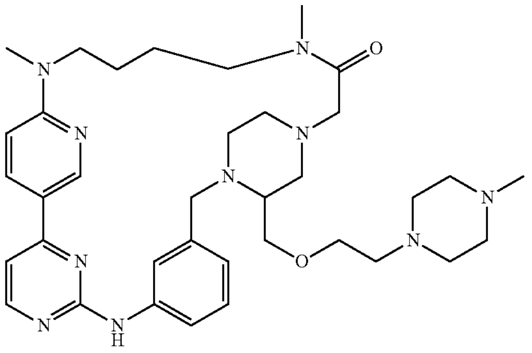

Compound_2

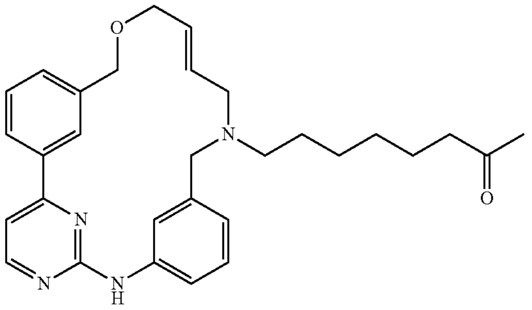

-continued

Compound_3

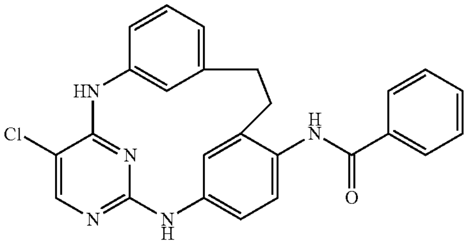

Compound_4

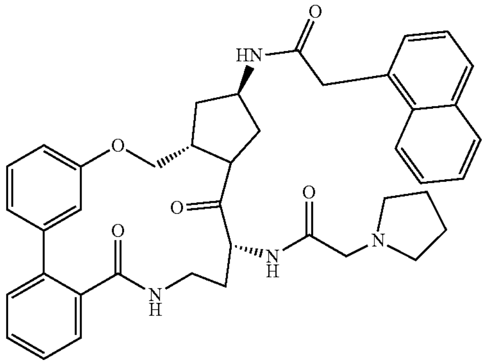

At present, macrocyclic kinase inhibitors used as candidate drugs, especially anti-tumor drugs, have entered various stages of clinical trial, and have shown a good application prospect. How to explore the indications of these compounds and further reduce the related potential side effects requires the development of clinical research on one hand, and also requires more various new kinase inhibitors with stronger effects on the other hand.

SUMMARY

Aiming at the shortcomings of the existing drugs, the invention provides an N-macrocyclic amide compound, or an isomer, a diastereomer, an enantiomer, a prodrug or a pharmaceutically acceptable salt thereof, wherein a structure of the N-macrocyclic amide compound is shown in a general structural formula (I) or a general structural formula (II):

Formula (I)

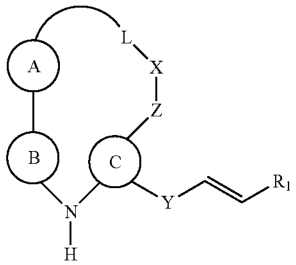

-continued

Formula (II)

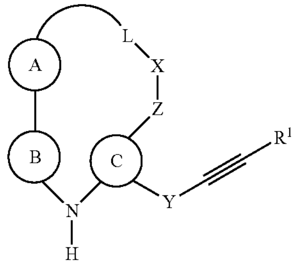

in the general structural formula (I) or the general structural formula (II),

L is a group represented by the following formula:

$-L^1-L^2-$, one end of $L^1$ in the formula is connected to A group, and one end of $L^2$ is connected to X group;

$L^1$ is selected from: a covalent bond, alkyl, —O—, —S—, —N($R^2$)—, alkyl-O—, —O-alkyl, alkyl-O-alkyl, alkyl-S—, —S-alkyl, alkyl-S-alkyl, alkyl-N($R^2$)—, —N($R^2$)-alkyl, or alkyl-N($R^2$)-alkyl;

$L^2$ is selected from: a covalent bond, alkyl, alkyl-CH═CH—, or —CH═CH-alkyl;

X is selected from: a covalent bond, —O—, —S—, or —N($R^2$)—;

Y is selected from: —O—, —S—, —N($R^2$)—, —N($R^2$)—CO—, —O-alkyl, —S-alkyl, —N($R^2$)-alkyl, or —N($R^2$)—CO-alkyl;

Z is selected from: a covalent bond or alkyl, wherein one or more carbons in a carbon chain of the alkyl can be substituted by a heteroatom;

$R^1$ group is selected from: H, alkyl, haloalkyl, cycloalkyl, heterocycloalkyl, aryl, heteroaryl, cycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, amino, alkylamino, aminoalkyl, carboxy, alkylcarboxy, acylamino, alkylacylamino, alkylsulfonyl, or alkylacyl, wherein each group can optionally be substituted;

or, R group is selected from one of the following groups:

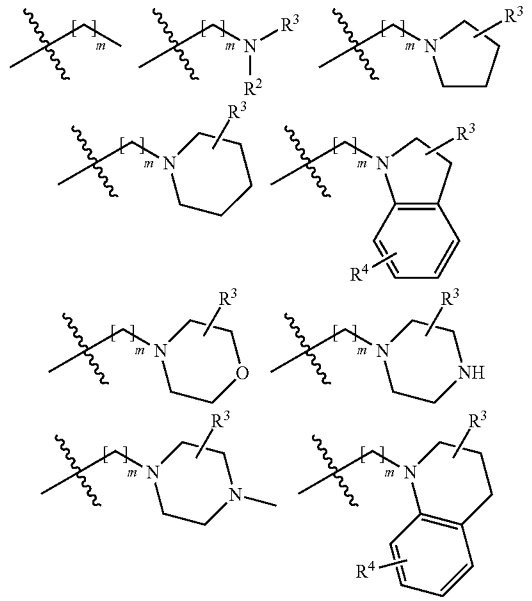

-continued

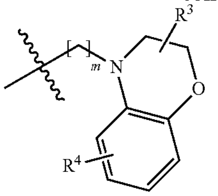
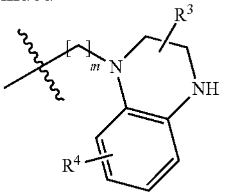
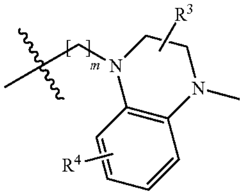
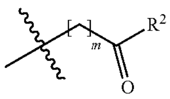
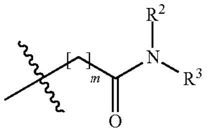
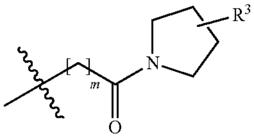
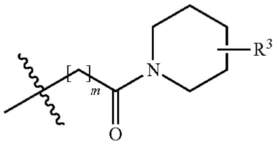
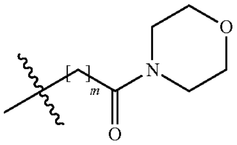
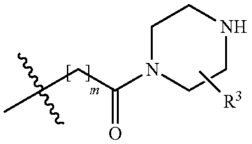
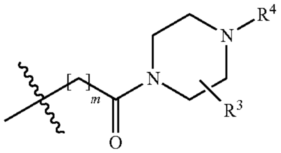
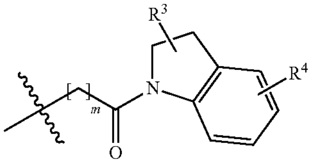
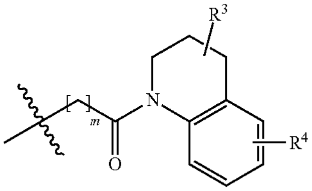
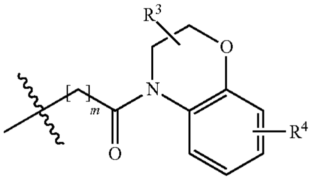
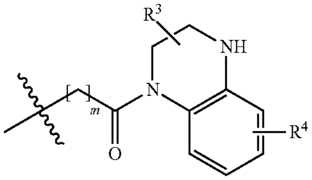
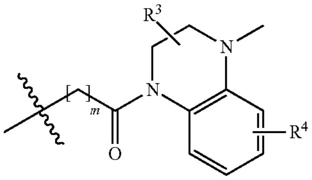

wherein m represents 0 to 3;

$R^2$, $R^3$, and $R^4$ are each independently selected from: H, alkyl, haloalkyl, cycloalkyl, heterocycloalkyl, aryl, heteroaryl, cycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, amino, alkylamino, aminoalkyl, carboxy, alkylcarboxy, acylamino, alkylacylamino, alkylsulfonyl, or acyl, wherein each group can optionally be substituted;

A group is selected from:

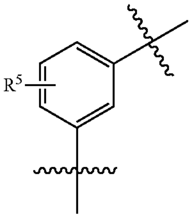

, $R^5$ group is selected from the following groups: H, halogen, alkyl, haloalkyl, heteroalkyl, cycloalkyl, cycloalkenyl, heterocycloalkyl, aryl, heteroaryl, cycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, alkoxy, amino, alkylamino, aminoalkyl, acylamino, alkylsulfonyl, or acyl, wherein each group can optionally be substituted;

B group is selected from one of the following groups:

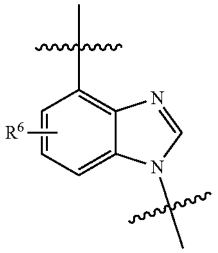
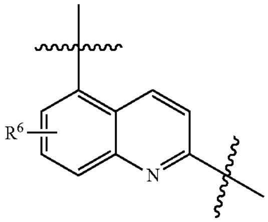
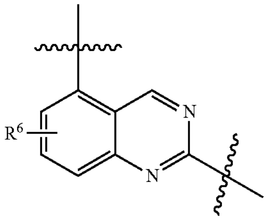
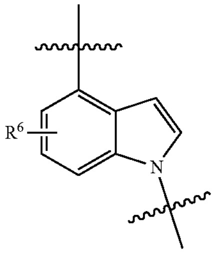
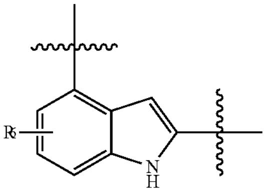
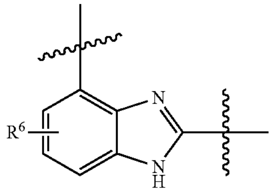

-continued

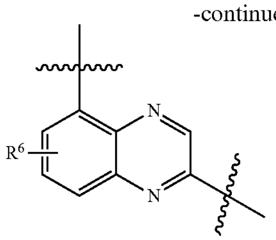

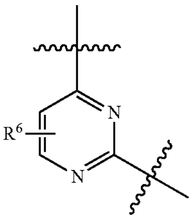, $R^5$ and $R^6$ groups are each independently selected from: H, halogen, alkyl, haloalkyl, heteroalkyl, cycloalkyl, cycloalkenyl, heterocycloalkyl, aryl, heteroaryl, cycloalkylalkyl, arylalkyl, heteroarylalkyl, cycloalkyl-heteroalkyl, heterocycloalkylheteroalkyl, heteroaryl-heteroalkyl, arylheteroalkyl, hydroxy, hydroxyalkyl, alkoxy, amino, alkylamino, aminoalkyl, carboxy, alkyl-carboxy, acylamino, alkylacylamino, alkylsulfonyl, or acyl, wherein each group can optionally be substituted;

C group is selected from:

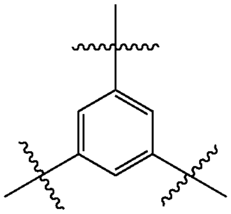

or

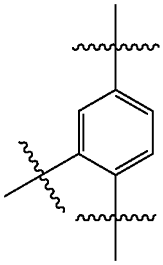, one of the ends of the formula of C is connected to Y group.

According to the compounds with the general structural formula (I) and the general structural formula (II) in the present invention, $L^1$ is selected from alkyl, wherein one or more carbons in a carbon chain of the alkyl can be substituted by a heteroatom;

$L^2$ is preferably selected from: —C1-C5 alkyl or —CH═CH—(C1-C5 alkyl);

Y is preferably selected from: —O—, —O-alkyl, —N($R^2$)-alkyl, or —N($R^2$)—CO-alkyl;

Z is preferably selected from C1-C2 alkyl;

$R^1$ is preferably selected from one of the following groups:

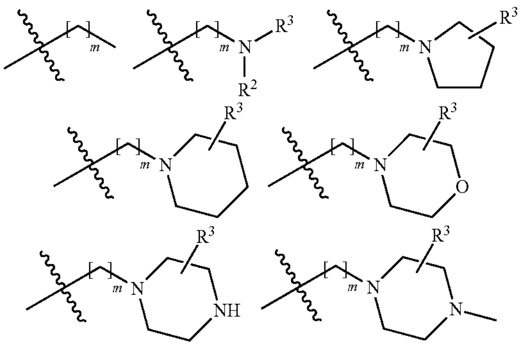

-continued

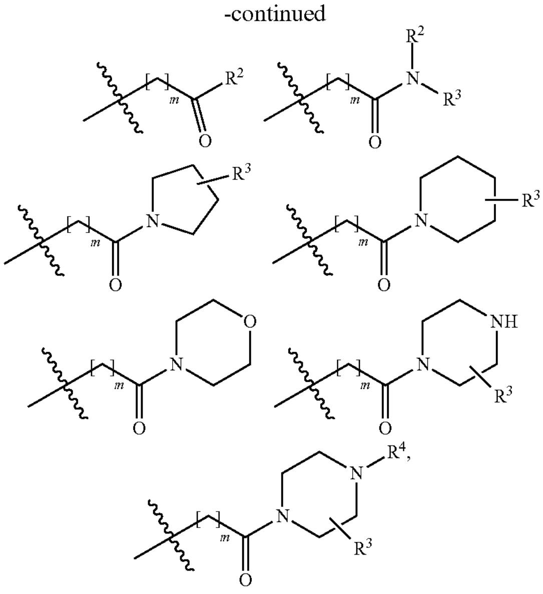

more preferably selected from one of the following groups:

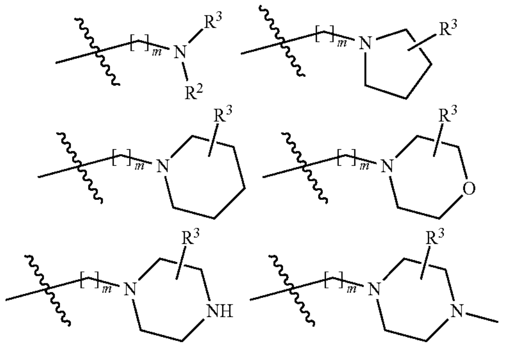, wherein m represents 0 to 3;

B group is preferably selected from one of the following groups:

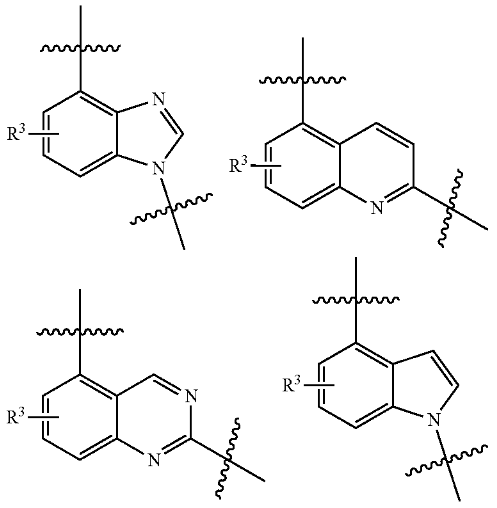

-continued
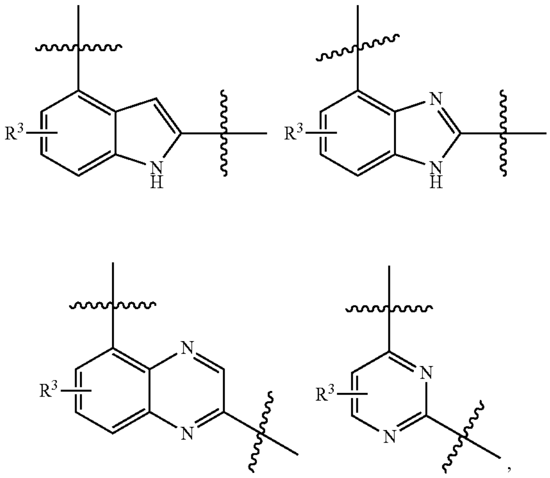
more preferably selected from:
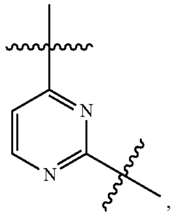 [SMILES: *c1ccnc(*)n1]
The compounds with the general structural formula (I) and the general structural formula (II) in the present invention comprise the following compounds:
XIII-1
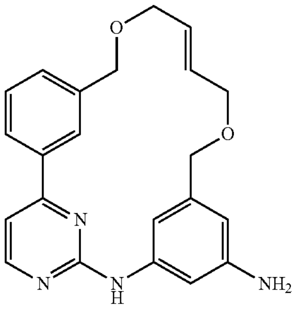 [SMILES: Nc1cc2cc(c1)Nc1nccc(n1)-c1cccc(c1)COC/C=C/COC2]
XIII-2
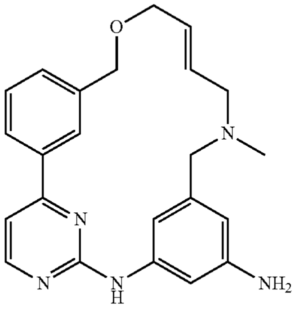 [SMILES: CN1C/C=C/COCc2cccc(c2)-c2ccnc(n2)Nc2cc(N)cc(c2)C1]
-continued
XVI-1
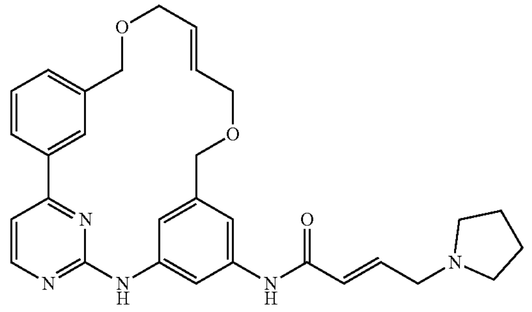 [SMILES: O=C(/C=C/CN1CCCC1)Nc1cc2cc(c1)Nc1nccc(n1)-c1cccc(c1)COC/C=C/COC2]
XVI-2
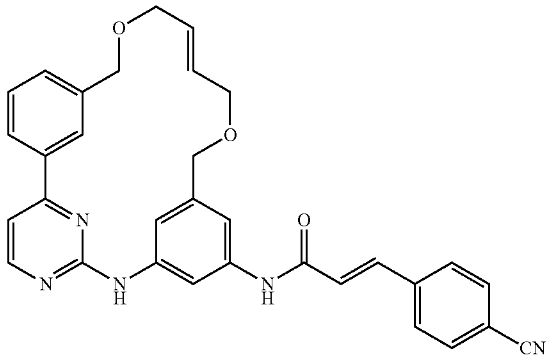 [SMILES: N#Cc1ccc(/C=C/C(=O)Nc2cc3cc(c2)Nc2nccc(n2)-c2cccc(c2)COC/C=C/COC3)cc1]
XVI-3
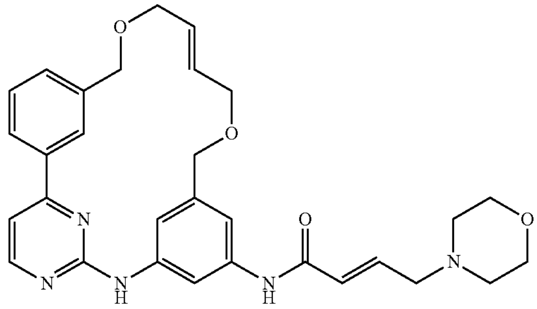 [SMILES: O=C(/C=C/CN1CCOCC1)Nc1cc2cc(c1)Nc1nccc(n1)-c1cccc(c1)COC/C=C/COC2]
XVI-4
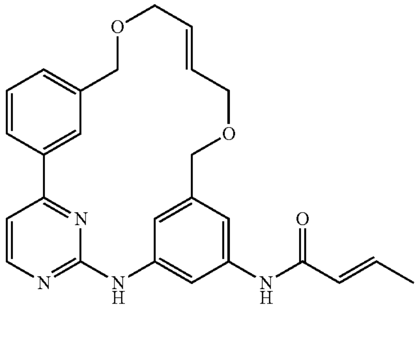 [SMILES: C/C=C/C(=O)Nc1cc2cc(c1)Nc1nccc(n1)-c1cccc(c1)COC/C=C/COC2]

-continued
XVI-5
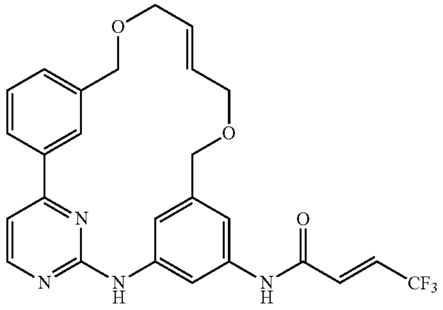 [SMILES: O=C(/C=C/C(F)(F)F)Nc1cc2cc(c1)Nc1nccc(n1)-c1cccc(c1)COC/C=C/COC2]
XVI-6
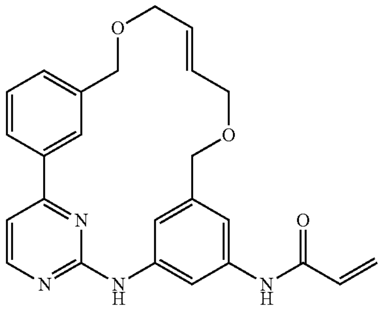 [SMILES: C=CC(=O)Nc1cc2cc(c1)Nc1nccc(n1)-c1cccc(c1)COC/C=C/COC2]
XVI-7
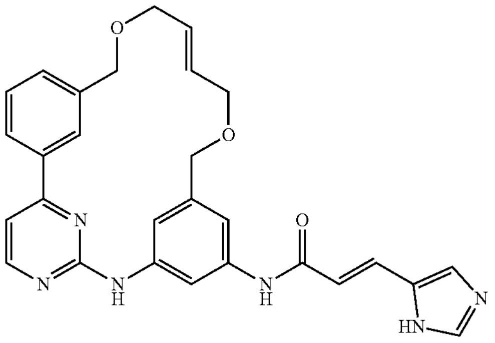
XVI-8
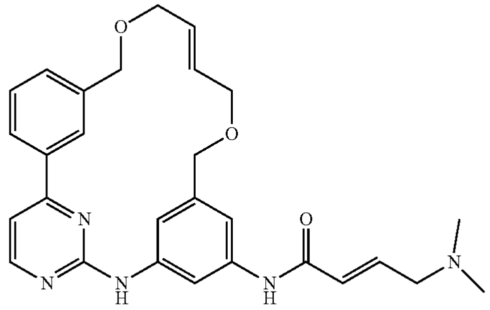
XVI-9
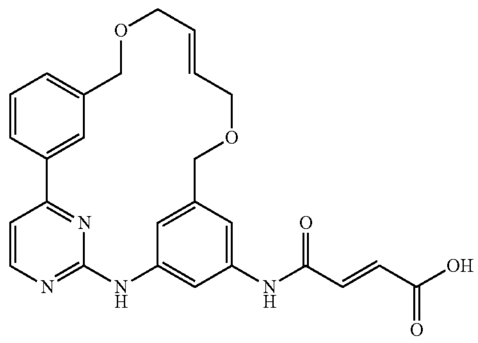
-continued
XVI-10
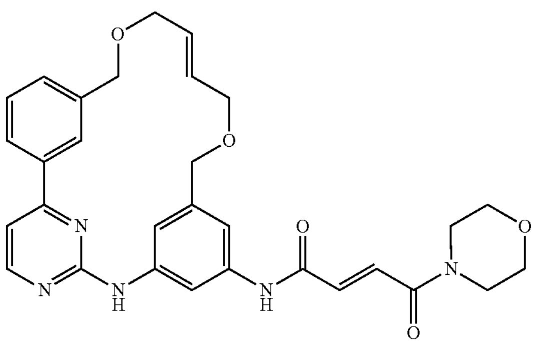
XVI-11
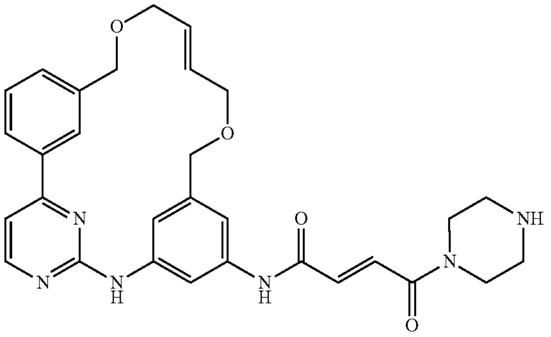
XVI-12
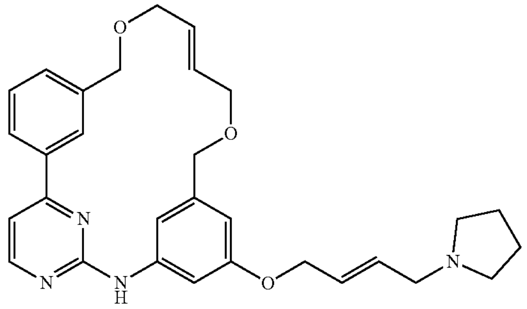
XVI-13
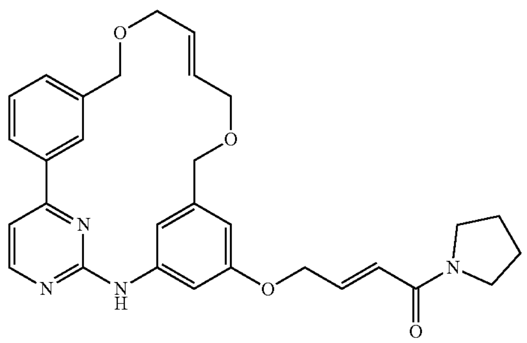

-continued
XVI-14
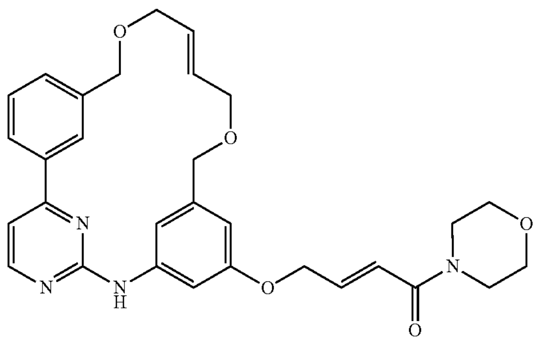
XVI-15
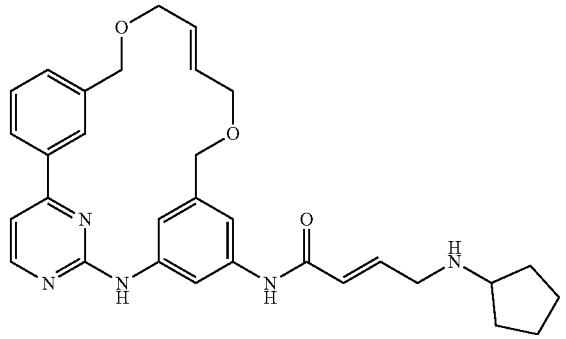
XVI-16
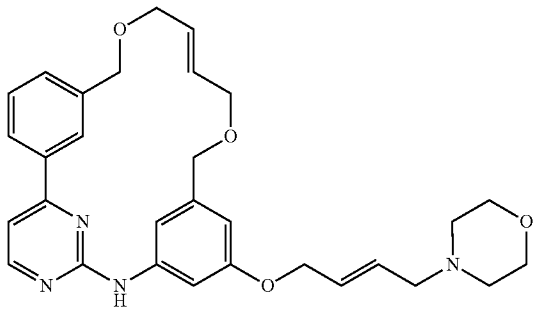
XVI-17
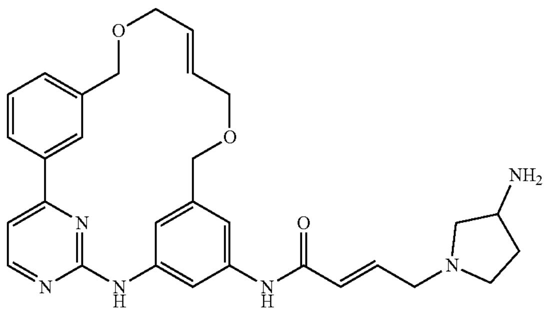
-continued
XVI-18
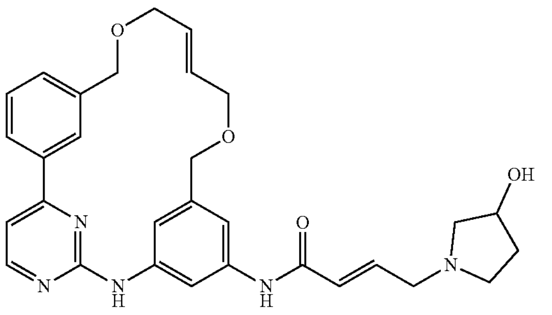
XVI-19
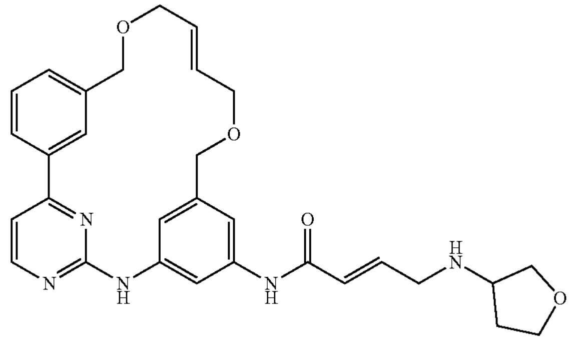
XVI-20
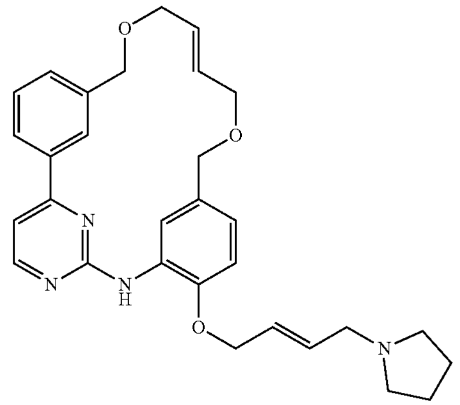
XVI-21
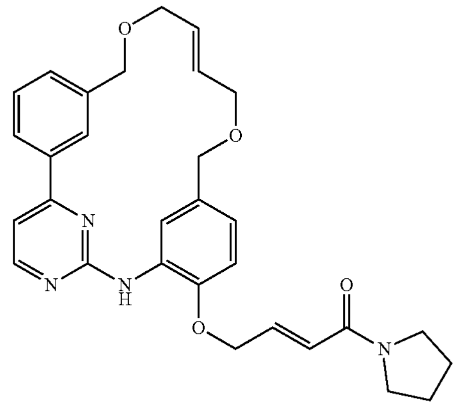

-continued
XVI-22
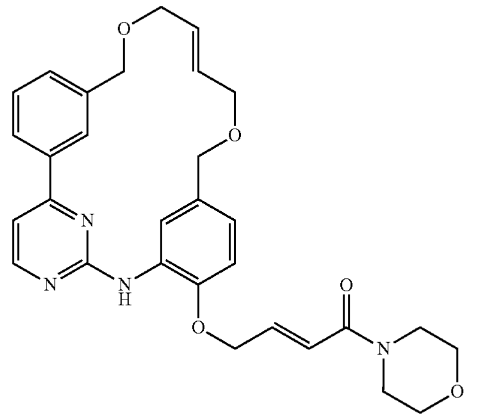
XVI-23
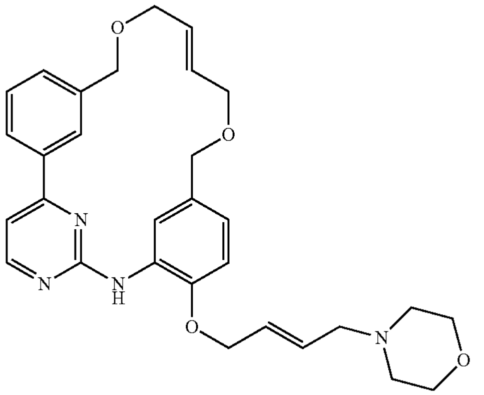
XVI-24
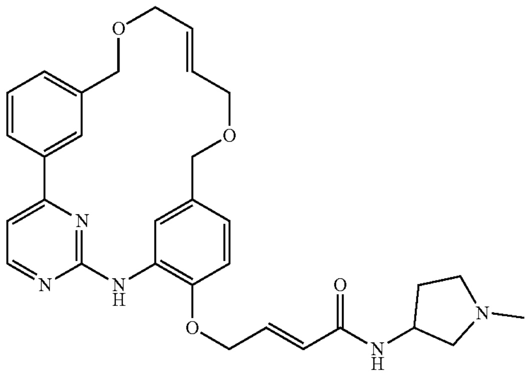
XVI-25
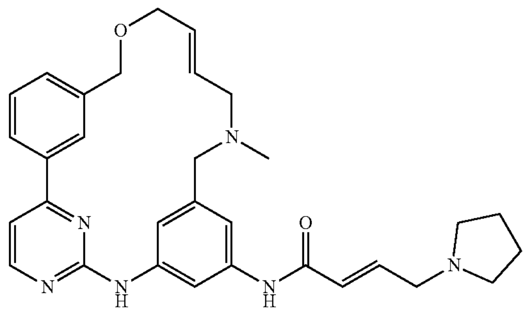
-continued
XVI-26
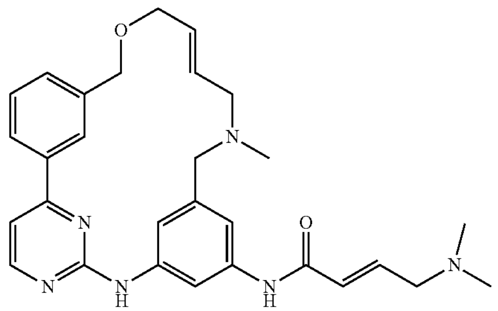
XVI-27
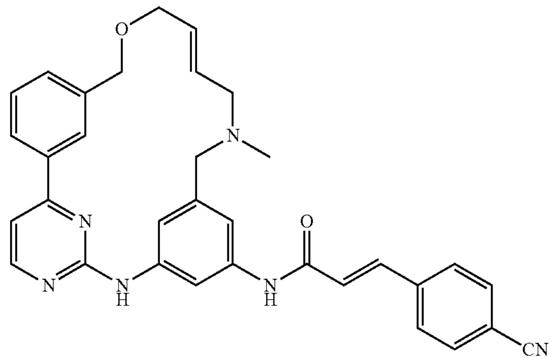
XVI-28
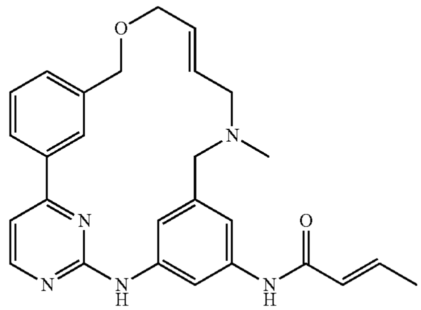
XVI-29
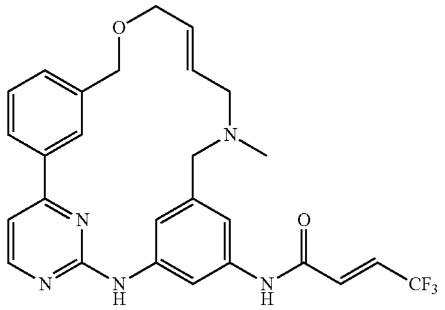

-continued
XVI-30
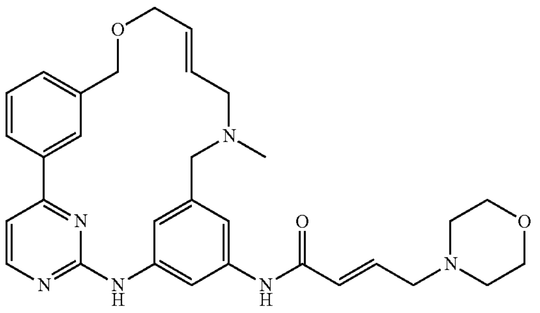
XVI-31
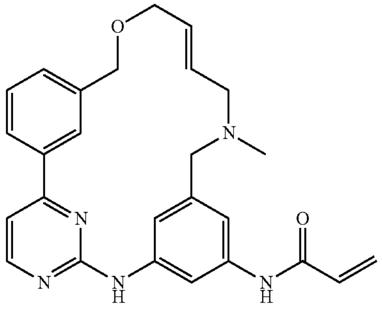
XVI-32
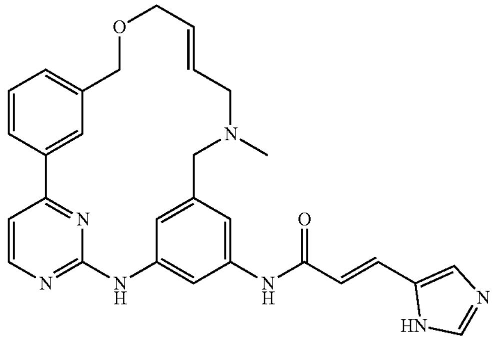
XVI-33
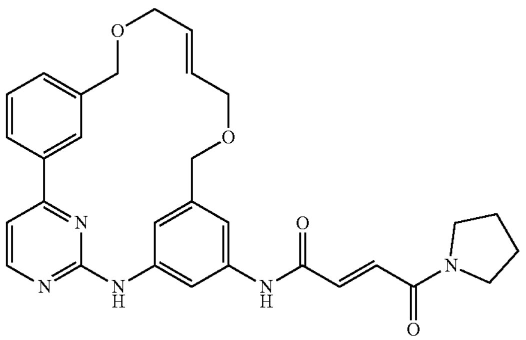
-continued
XVI-34
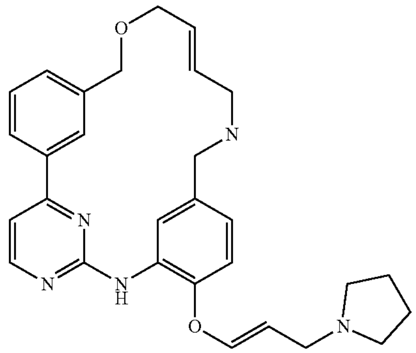
XVII-1
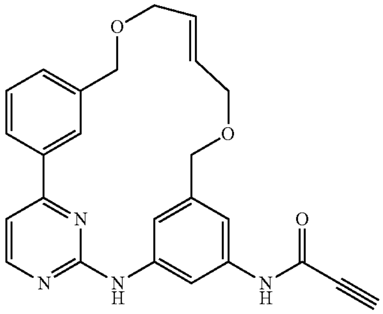
XVII-2
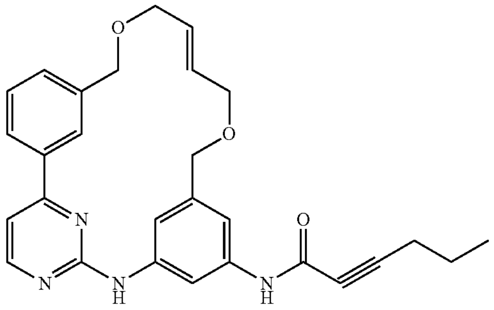
XVII-3
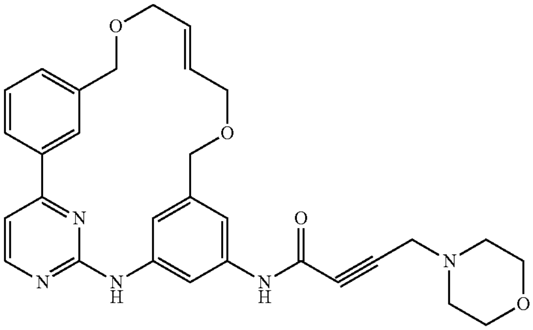

-continued

XVII-4

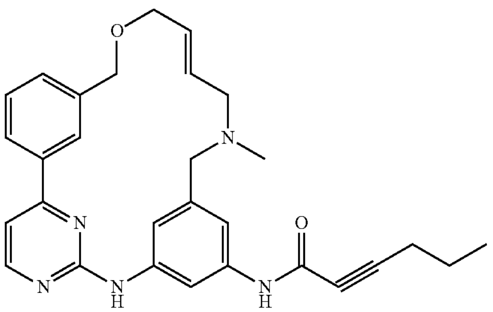

XVII-5

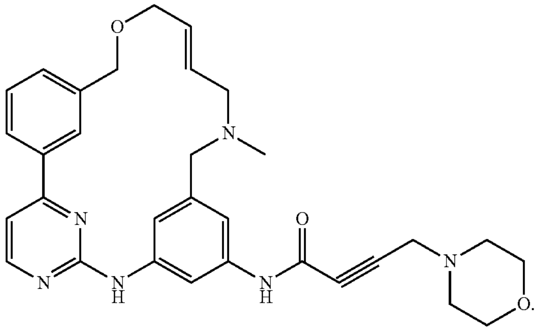

As used herein, the term "unsubstituted" means that there is no substituent or the only substituent is H.

As used herein, the term "optionally substituted" means that the group may be further substituted or fused by one or more non-hydrogen substituents. These substituents are independently selected from one or more of the following groups: halogen, =O, =S, —CN, —$NO_2$, —$CF_3$, —$OCF_3$, alkyl, haloalkyl, heteroalkyl, cycloalkyl, cycloalkenyl, heterocycloalkyl, aryl, heteroaryl, cycloalkylalkyl, arylalkyl, heteroarylalkyl, cycloalkylheteroalkyl, heterocycloalkylheteroalkyl, heteroarylheteroalkyl, arylheteroalkyl, hydroxy, alkoxy, hydroxyalkyl, amino, alkylamino, aminoalkyl, acylamino, alkylsulfonyl and acyl.

"Halogen" refers to fluorine, chlorine, bromine and iodine.

As a group or part of a group, "alkyl" is a C1-C14 straight-chain or branched-chain aliphatic hydrocarbon group, unless otherwise specified.

"Heteroatom" refers to S, O and N atoms.

"Heteroalkyl" refers to C1-C14 straight-chain or branched-chain alkyl, wherein one or more carbons are substituted by heteroatoms, and the heteroatoms are defined as above.

"Cycloalkyl" refers to a saturated or partially saturated carboatomic ring of a monocyclic ring, a fused ring or a spirocyclic ring. A ring consisting of 3 to 9 carbon atoms is preferred. The group may be a terminal group or a bridging group.

"Cycloalkenyl" refers to a non-aromatic monocyclic or polycyclic ring system. At least one carbon-carbon double bond is contained and each ring preferably has 5 to 10 carbon atoms. The group may be a terminal group or a bridging group.

"Heterocycloalkyl" refers to cycloalkyl containing at least one heteroatom. Preferably, the cycloalkyl contains 1 to 3 heteroatoms. Preferably, the ring is a 3 to 14-membered ring, and more preferably, the ring is a 4 to 7-membered ring. The cycloalkyl and the heteroatom are defined as above. The group may be a terminal group or a bridging group.

As a group or part of a group, "aryl" refers to an aromatic carbocyclic ring of a monocyclic ring or a fused polycyclic ring capable of being optionally substituted, and each ring preferably contains 5 to 12 atoms. The group may be a terminal group or a bridging group.

As a group or part of a group, "heteroaryl" refers to a group containing an aromatic ring, which has one or more heteroatoms in ring atoms of an aromatic ring. The heteroatom is defined as above. The group may be a terminal group or a bridging group.

"Cycloalkylalkyl" refers to cycloalkyl-alkyl, wherein the cycloalkyl and the alkyl are as described above, and the group may be a terminal group or a bridging group.

"Arylalkyl" refers to an (aryl-alkyl)-group. The aryl and the alkyl are defined herein. The group may be a terminal group or a bridging group.

"Heteroarylalkyl" refers to a (heteroaryl-alkyl)-group. The aryl and the alkyl are defined herein. The group may be a terminal group or a bridging group.

"Arylheteroalkyl" refers to an (aryl-heteroalkyl)-group. The aryl and the heteroalkyl are defined herein. The group may be a terminal group or a bridging group.

"Cycloalkylheteroalkyl" refers to a (cycloalkyl-heteroalkyl)-group. The cycloalkyl and the heteroalkyl are defined herein. The group may be a terminal group or a bridging group.

"Heterocycloalkylheteroalkyl" refers to a (heterocycloalkyl-heteroalkyl)-group. The heterocycloalkyl and the heteroalkyl are defined herein. The group may be a terminal group or a bridging group.

"Heteroarylheteroalkyl" refers to a (heteroaryl-heteroalkyl)-group. The heteroaryl and the heteroalkyl are defined herein. The group may be a terminal group or a bridging group.

"Aminoalkyl" refers to an (amino-alkyl)-group. The alkyl is defined herein. The group may be a terminal group or a bridging group.

"Alkoxy" refers to —O-alkyl, wherein the alkyl is as defined herein. The alkoxy is preferably C1-C6 alkoxy. The group may be a terminal group or a bridging group.

Unless otherwise specified, "alkylamino" refers to monoalkylamino and dialkylamino. "Monoalkylamino" refers to —NH-alkyl, wherein the alkyl is defined as above. "Dialkylamino" refers to —N$(alkyl)_2$, wherein each alkyl may be the same or different, and meets the definition of the alkyl herein. The group may be a terminal group or a bridging group.

Unless otherwise specified, "arylamino" comprises monoarylamino and diarylamino. "Monoarylamino" refers to aryl —NH—, wherein the aryl is defined as above. "Diarylamino" refers to $(aryl)_2$N—, wherein each aryl may be the same or different, and meets the definition of the aryl herein. The group may be a terminal group or a bridging group.

"Acyl" refers to alkyl —CO—, wherein the alkyl is as defined herein. The group may be a terminal group or a bridging group.

"Acylamino" refers to an (acyl-amino)-group, wherein the acyl and the amino are as defined herein. The group may be a terminal group or a bridging group.

"Alkylsulfonyl" refers to —S$(O)_2$-alkyl, wherein the alkyl is as defined herein. The group may be a terminal group or a bridging group.

"Hydroxyalkyl" refers to an -alkyl-hydroxy group. The alkyl is as defined herein.

The term “pharmaceutical salt” or “pharmaceutically acceptable salt” refers to a salt of a compound identified above that retains required biological activity, comprising pharmaceutically acceptable acid addition salts and base addition salts. Acid addition salts of compounds shown in a general structural formula (I) and a general structural formula (II) may be prepared from an inorganic or organic acid. The inorganic acid may comprise, but is not limited to, hydrochloric acid, phosphoric acid and sulfuric acid. The suitable organic acid may comprise, but is not limited to, formic acid, acetic acid, propionic acid, succinic acid, alkyl sulfonic acid, glycollic acid, gluconic acid, lactic acid, malic acid, citric acid, tartaric acid, fumaric acid, maleic acid and aryl sulfonic acid. The base addition salts of the compounds shown in the general structural formula (I) comprise, but are not limited to, metal salts prepared from lithium, sodium, potassium, calcium, magnesium, aluminum and zinc, and organic salts prepared from organic bases such as choline, morpholine and diethanolamine.

The compounds shown in the general structural formula (I) and the general structural formula (II) comprise isomer forms, comprising a diastereomer, an enantiomer, a tautomer, and a geometric isomer of an “E” or “Z” configurational isomer or a mixture of E and Z isomers. Some compounds in the embodiments may exist as single stereoisomers, racemes and/or mixtures of enantiomers and/or diastereomers.

In addition, the general structural formula (I) and the general structural formula (II) should comprise solvated and unsolvated forms of the compounds.

In the general structural formula (I) and the general structural formula (II), when A group is

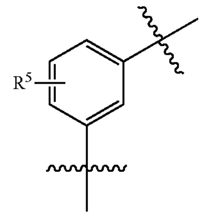

,

B group is N

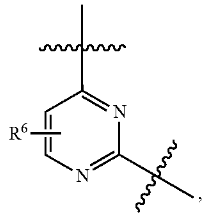

,

C group is

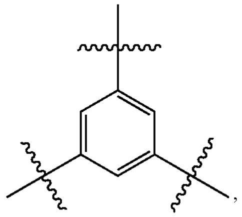

,

X is —O—, Y is —NH—CO—, $L^1$ is alkyl-O—, $L^2$ is alkyl-CH═CH—, and Z is alkyl, the corresponding compounds may be synthesized by a method shown in a synthesis route 1:

Synthesis Route 1

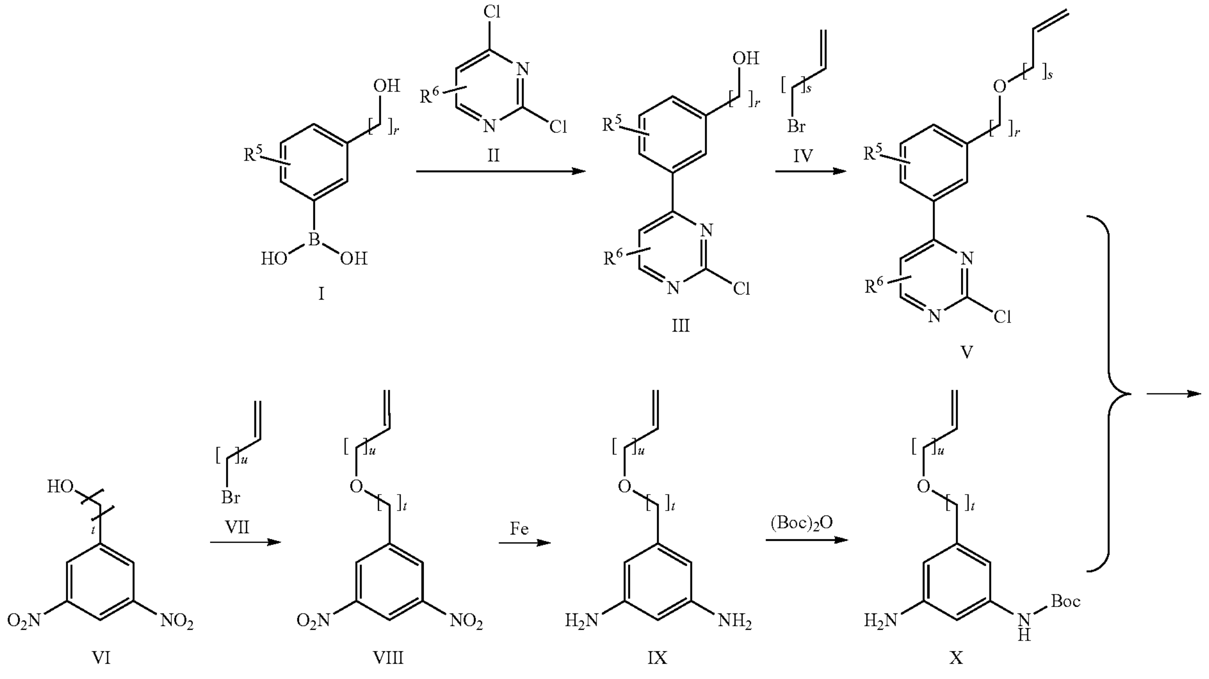

-continued

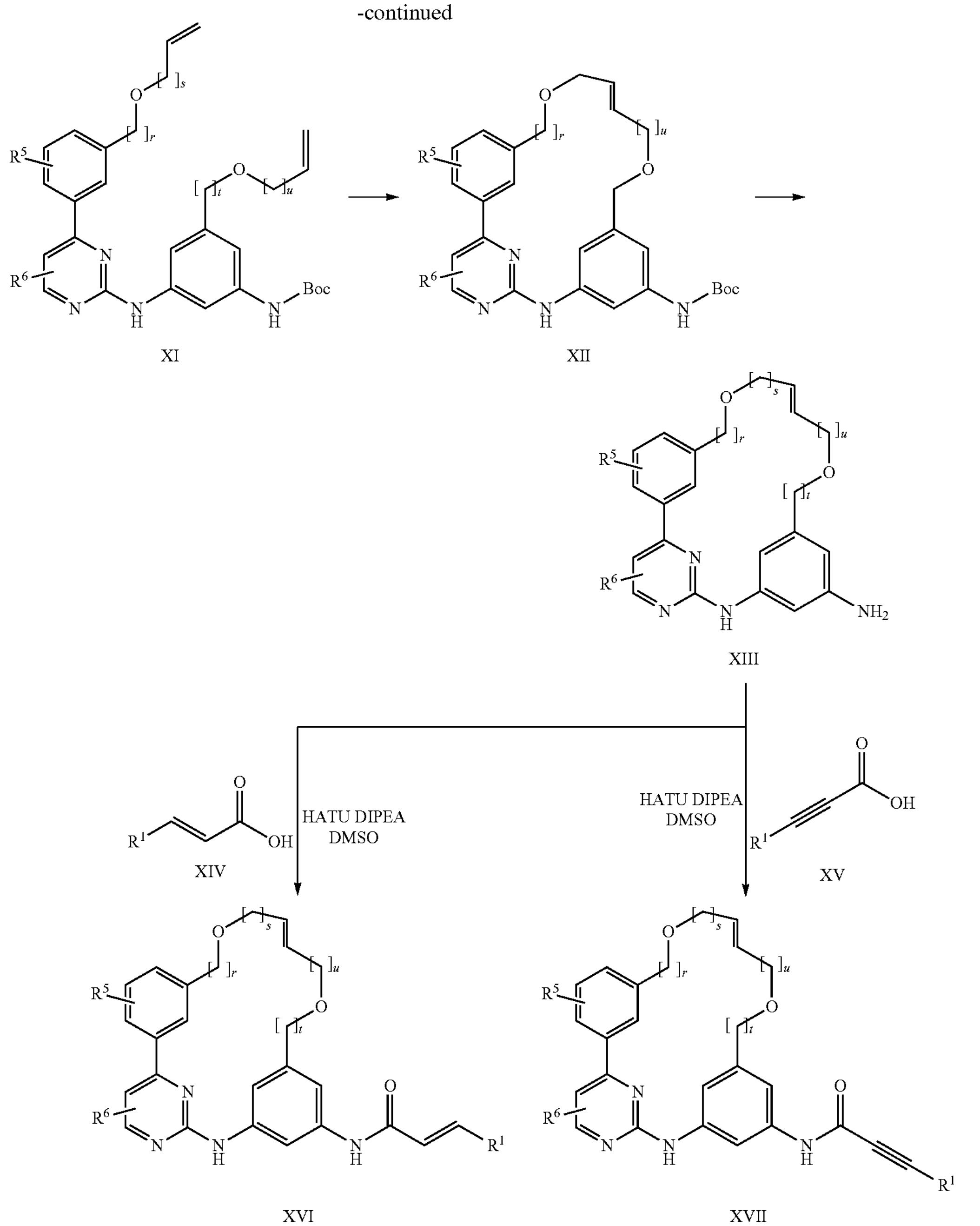

XI XII XIII XIV XV XVI XVII

Specifically, as shown in the synthesis route 1, a suitable boron compound I is selected to react with a pyrimidine derivative II with suitable substituents under Suzuki coupling conditions to obtain a biaryl compound III. In the presence of a suitable base, the compound III and an alkenyl bromide IV undergo a condensation reaction to obtain a compound V. On the other hand, a proper compound VI is selected as a raw material to condensate with a pyrimidine derivative VII with corresponding substituents to obtain an intermediate VIII. X is obtained after reduction and single protection. The intermediate V obtained above is condensed with compound X under basic conditions to obtain a compound intermediate XI. The intermediate XI undergoes Ring-Closing Metathesis catalyzed by Grubbs II catalyst to obtain a macrocyclic intermediate XII. A protective group was removed under acidic conditions to obtain a compound XIII. Under the action of suitable reagents and solvents, the compound XIII reacts with compounds XIV and XV to obtain target compounds XVI and XVII respectively.

Wherein, $R^1$, $R^5$ and $R^6$ are as defined above, and r, s, t and u each independently represent 0 to 5.

The present invention further provides an application of the N-macrocyclic amide compound, or an isomer, a diastereomer, an enantiomer, a prodrug or a pharmaceutically acceptable salt thereof according to any one of the technical solutions above as a medicament.

The present invention further provides a pharmaceutical composition, comprising the N-macrocyclic amide compound according to any one of the technical solutions above, or an isomer, a diastereomer, an enantiomer, a prodrug or a pharmaceutically acceptable salt thereof, and one or more of a pharmaceutically acceptable diluent, a pharmaceutically acceptable excipient, and a pharmaceutically acceptable carrier.

The present invention further provides use of the N-macrocyclic amide compound according to any one of the technical solutions above, or an isomer, a diastereomer, an enantiomer, a prodrug or a pharmaceutically acceptable salt thereof, or the pharmaceutical composition according to the technical solution above, optionally in combination with another medicament or a plurality of medicaments, for preparing a medicament for inhibiting one kinase or a plurality of kinases.

In the use of the present invention, the kinase is selected from: CDK2, CDK3, CDK4, CDK5, CDK6, CDK9, PCTAIREK, PCTAIRE2, PCTAIRE3, CAK/MO15, Dm2, Dm2c, Ddcdc2, DdPRK, LmmCRKK, PfC2R, EhC2R, CfCdc2R, cdc2+, CDC28, PHO85, KIN28, FpCdc2, MsCdc2B, OsC2R, PDGFR-b, PDGFR-a, CSF1R, c-kit, Flk2, FLT1, FLT2, FLT3, FLT4, TYK2, JAK1, JAK2, HOP, or functional equivalents thereof.

The present invention also provides use of the N-macrocyclic amide compound according to any one of the technical solutions above, or an isomer, a diastereomer, an enantiomer, a prodrug or a pharmaceutically acceptable salt thereof, or the pharmaceutical composition according to the technical solution above, for preparing a medicament for the treatment of a disease caused by, associated with or accompanied by disruption of cell proliferation and/or angiogenesis.

In the use of the present invention, the disease may be a proliferative disease.

In the use of the present invention, the proliferative disease may be a cancer.

In the use of the present invention, the proliferative disease may be selected from: myeloproliferative diseases (chronic idiopathic myelofibrosis, polycythemia vera, essential thrombocythemia, and chronic myelogenous leukemia), myeloid metaplasia, chronic myelomonocytic leukemia, acute myelogenous leukemia, juvenile myelomonocytic leukemia, acute promyelocytic leukemia, acute lymphoblastic leukemia, acute erythroblastic leukemia, acute B-cell leukemia, leukocytosis, Hodgkin's disease, B-cell lymphoma, acute T-cell leukemia, breast cancer, ovarian cancer, colon cancer, prostate cancer, melanoma, myelodysplastic syndrome, keloid, retinoblastoma, breast malignant tumor, colon malignant tumor, endometrial hyperplasia, osteosarcoma, squamous cell carcinoma, non-small cell lung cancer, hepatocellular carcinoma, pancreatic malignant tumor, myelogenous leukemia, cervical cancer, fibroma, colonic adenocarcinoma, glioma, glioblastoma, oligodendroglioma, lymphoma, restenosis, astrocytoma, bladder tumor, or musculoskeletal tumor.

In the use of the present invention, the proliferative disease is selected from: prostate cancer, retinoblastoma, breast malignant tumor, colon malignant tumor, endometrial hyperplasia, osteosarcoma, squamous cell carcinoma, non-small cell lung cancer, melanoma, hepatocellular carcinoma, pancreatic malignant tumor, myelogenous leukemia, cervical cancer, fibroma, colonic adenocarcinoma, T-cell leukemia, glioma, glioblastoma, oligodendroglioma, lymphoma, ovarian cancer, restenosis, astrocytoma, bladder tumor, musculoskeletal tumor, or Alzheimer's disease.

In the use of the present invention, the proliferative disease is selected from: acute myelogenous leukemia, acute promyelocytic leukemia, acute lymphoblastic leukemia, myelodysplastic syndrome, leukocytosis, juvenile myelomonocytic leukemia, acute B-cell leukemia, chronic myelogenous leukemia, acute T-cell leukemia, myeloproliferative disease, or chronic myelomonocytic leukemia.

DESCRIPTION OF EXEMPLARY EMBODIMENTS

In the following embodiments, unless otherwise specified, all the temperature units were degree Celsius.

Various starting materials and reagents were purchased from the market. Suppliers comprised, but were not limited to: Aldrich Chemical Company, Lancaster Synthesis Ltd, and the like. Unless otherwise indicated, commercially available starting materials and reagents were used without further purification.

Glass wares were dried in an oven and/or heated for drying. The reaction was traced on a glass silica gel −60 F254 plate (0.25 mm) (TLC). Analytical thin layer chromatography was carried out with appropriate solvent ratio (v/v). The end point of the reaction was the moment when the starting material of the reaction on TLC is exhausted.

$^1$H NMR spectrum was determined by Bruker instrument (300 MHz or 400 MHz), and chemical shift was expressed in ppm. Chloroform was used as a reference standard (7.25 ppm) or tetramethylsilane internal standard (0.00 ppm). Other solvents commonly used in NMR could also be used as needed. $^1$H-NMR was expressed as follows: s=singlet, d=doublet, t=triplet, m=multiplet, br=broadened, dd=doublet of doublets, and dt=doublet of triplets. If a coupling constant was provided, it was in the unit of Hz.

A mass spectrum was determined by MS, and an ionization method might be ESI or APCI.

The following embodiments were only used to illustrate the synthesis method of the specific compounds invented. However, there were no restrictions on the synthesis method. Compounds not listed in the embodiments may also be prepared by the same synthesis route and method as below, selecting appropriate starting materials and slightly adjusting appropriate common sense reaction conditions where necessary.

Example 1

Synthesis Route 1

(1) (3-(2-chloro-pyrimidin-4-yl)phenyl)methanol (III-1)

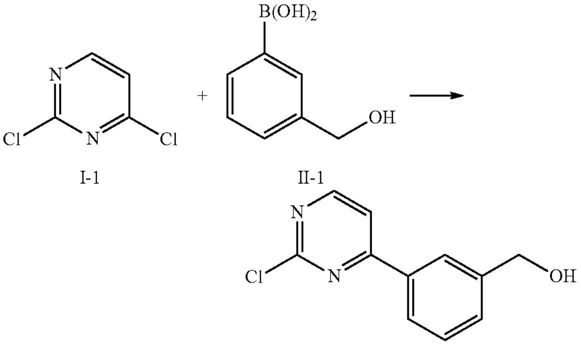

I-1 II-1 III-1

| Reaction material | Feeding amount | Molecular weight | Mole number(mmol) | Eq |
|---|---|---|---|---|
| 2,4-dichloropyrimidine (I-1) | 30.0 g | 149.0 | 201.3 | 1 |
| 3-hydroxymethyl phenylboronic acid (II-1) | 35.2 g | 152.0 | 231.5 | 1.15 |
| sodium carbonate | 32.0 g | 106.0 | 302.0 | 1.5 |
| Tetrakis(triphenylphosphine) palladium | 11.6 g | 1155.6 | 10.1 | 0.05 |
| Ethylene glycol dimethyl ether | 300 mL | — | — | — |

Saturated solution of compound 3-hydroxymethyl phenylboronic acid (II-1, 35.2 g, 231.5 mmol), 2,4-dichloropyrimidine (I-1, 30.0 g, 201.3 mmol), sodium carbonate (32.0 g, 302.0 mmol), tetrakis(triphenylphosphine) palladium (11.6 g, 10.1 mmol), and ethylene glycol dimethyl ether (300 mL) were added into a reaction flask, and then replaced three times with nitrogen gas for protection. The temperature was raised to 80° C. to react for 3 hours. The reaction system was detected by TLC plate (PE/EA=2:1), and the raw materials disappeared under an ultraviolet analyzer at 254 nm, and the products no longer increased, so it was judged that the reaction was terminated. Saturated ammonium chloride solution was added to quench the reaction, then 100 mL of dichloromethane was added, and the system was stirred for 10 minutes. The system was allowed to settle for layering, the organic phases were collected. The aqueous phase was extracted with dichloromethane (50 mL×2), the organic phases were combined, and the aqueous phase was discarded. The organic phases were washed with 50 mL of saturated sodium chloride solution, and the system was allowed to settle for layering, the aqueous phase was discarded, and the organic phases were dried with an appropriate amount of anhydrous sodium sulfate. After drying, the desiccant was filtered out, and the filtrate was concentrated to dryness under reduced pressure to obtain a residue. The residue was passed through a flash column (an elution system was ethyl acetate/petroleum ether, and a ratio was gradually increased from 1:20 to 1:3), and an eluent of a corresponding product was collected and concentrated to dryness under reduced pressure to obtain compound III-1 (39 g, 88.2%). $^1$H NMR (400 MHz, DMSO-$d_6$): δ8.67 (d, J=5.2 Hz, 1H), 8.09 (s, 1H), 7.97 (dd, J=1.4 and 6.8 Hz, 1H), 7.65 (d, J=5.2 Hz, 1H), 7.55-7.47 (m, 2H), 4.79 (d, J=6.0 Hz, 2H), 2.36 (t, J=6.0 Hz, 1H). MS (m/z): 243 (M Na)$^+$.

(2) 4-(3-((allyloxy)methyl)phenyl)-2-chloropyrimidine (V-1)

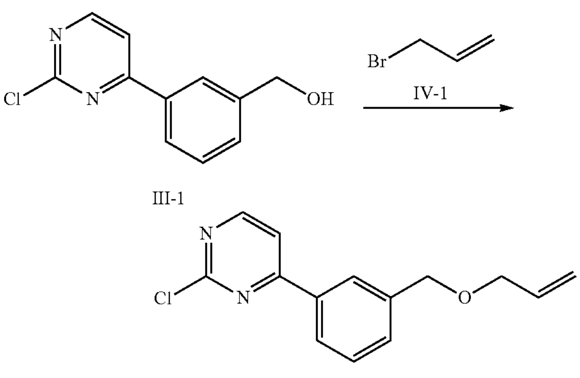

III-1

V-1

| Reaction material | Feeding amount | Molecular weight | Mole number (mmol) | Eq |
|---|---|---|---|---|
| III-1 | 5.0 g | 220.7 | 22.7 | 1 |
| 3-bromopropene (IV-1) | 25 mL | — | — | — |
| Potassium hydroxide | 2.5 g | 56.1 | 45.4 | 2 |
| Tetrabutylammonium iodide | 0.4 g | 369.4 | 1.1 | 0.05 |

Compound III-1 (5.0 g, 22.7 mmol), 3-bromopropene (IV-1, 25 mL), potassium hydroxide (2.5 g, 45.4 mmol) and tetrabutylammonium iodide (0.4 g, 1.1 mmol) were added into a reaction flask, and the mixture was stirred at room temperature overnight. The reaction system was detected by TLC plate (PE/EA=2:1), and the raw materials disappeared under an ultraviolet analyzer at 254 nm, and the products no longer increased, so it was judged that the reaction was terminated. 30 mL of water was added, and the system was stirred for 10 minutes. The system was allowed to settle for layering, the organic phases were collected. The aqueous phase was extracted with dichloromethane (20 mL×2), the organic phases were combined, and the aqueous phase was discarded. The organic phases were washed with 20 mL of saturated sodium chloride solution, and the system was allowed to settle for layering, the aqueous phase was discarded, and the organic phases were dried with an appropriate amount of anhydrous sodium sulfate. After drying, the desiccant was filtered out, and the filtrate was concentrated to dryness under reduced pressure to obtain a residue. The residue was passed through a flash column (an elution system was ethyl acetate/petroleum ether, and a ratio was gradually increased from 1:20 to 1:5), and an eluent of a corresponding product was collected and concentrated to dryness under reduced pressure to obtain compound V-1 (5 g, 84.7%). $^1$H NMR (400 MHz, DMSO-$d_6$): δ8.64-7.47 (m, 6H), 6.07-5.94 (m, 2H), 5.37-5.22 (m, 4H), 4.61 (s, 2H), 4.09 (d, 2H, J=10.8 Hz). MS (m/z): 261 (MH)$^+$.

(3) 1-((allyloxy)methyl)-3,5-dinitrobenzene (VIII-1)

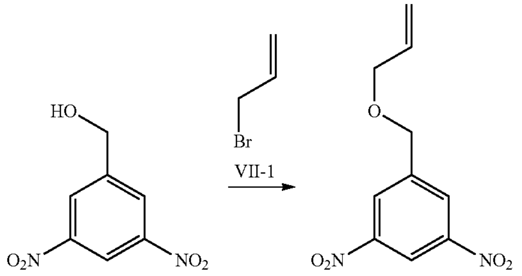

VI-1 VIII-1

| Reaction material | Feeding amount | Molecular weight | Mole number (mmol) | Eq |
|---|---|---|---|---|
| 3,5-dinitrobenzyl alcohol (VI-1) | 20.0 g | 198.1 | 119.1 | 1 |
| 3-bromopropene (VII-1) | 100 mL | — | — | — |
| Potassium hydroxide | 16.7 g | 56.1 | 297.8 | 2.5 |
| Tetrabutylammonium iodide | 2.2 g | 369.4 | 6.0 | 0.05 |

3,5-dinitrobenyl alcohol (VI-1, 20.0 g, 119.1 mmol), 3-bromopropene (VII-1, 100 mL), potassium hydroxide (16.7 g, 297.8 mmol) and tetrabutylammonium iodide (2.2 g, 6 mmol) were added into a reaction flask, and the mixture was stirred at room temperature overnight. The reaction system was detected by TLC plate (PE/EA=5:1), and the raw materials disappeared under an ultraviolet analyzer at 254 nm, and the products no longer increased, so it was judged that the reaction was terminated. 200 mL of water was added, and the system was stirred for 10 minutes. The system was allowed to settle for layering, the organic phases were collected. The aqueous phase was extracted with dichloromethane (50 mL×2), the organic phases were combined, and the aqueous phase was discarded. The organic phases were washed with 100 mL of saturated sodium chloride solution, and the system was allowed to settle for layering, the aqueous phase was discarded, and the organic phases were dried with an appropriate amount of anhydrous sodium sulfate. After drying, the desiccant was filtered out, and the filtrate was concentrated to dryness under reduced pressure to obtain a residue. The residue was passed through a flash column (an elution system was ethyl acetate/petroleum ether, and a ratio was gradually increased from 1:50 to 1:10), and an eluent of a corresponding product was collected and concentrated to dryness under reduced pressure to obtain compound VIII-1 (10.4 g, 43.3%).

(4) 5-((allyloxy)methyl)benzene-1,3-diamine (IX-1)

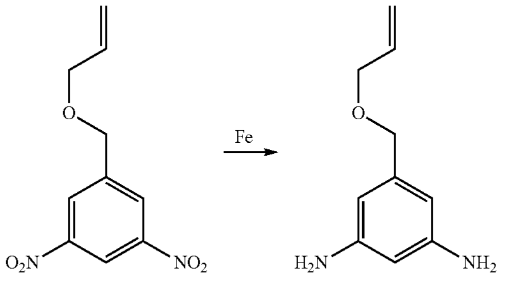

VIII-1 IX-1

| Reaction material | Feeding amount | Molecular weight | Mole number (mmol) | Eq |
|---|---|---|---|---|
| VIII-1 | 7.7 g | 238.2 | 32.4 | 1 |
| Iron powder | 10.9 g | 55.8 | 194.1 | 6 |
| Ammonium chloride | 20.6 g | 53.5 | 388.2 | 12 |
| Anhydrous ethanol | 85 mL | — | — | — |

Compound VIII-1 (7.7 g, 32.4 mmol) and anhydrous ethanol (85 mL) were added into a reaction flask, then heated to 50° C., and then an aqueous solution of iron powder (10.9 g, 194.1 mmol) and ammonium chloride (20.6 g, 388.2 mmol) were added into the reaction flask, and refluxed for reaction for 4 hours. The reaction system was detected by TLC plate (PE/EA=2:1), and the raw materials disappeared under an ultraviolet analyzer at 254 nm, and the products no longer increased, so it was judged that the reaction was terminated. The system was cooled to room temperature, and the iron powder was removed by suction filtration, and then the filtrate was concentrated to dryness under reduced pressure, and an obtained residue was added into water, then the pH was adjusted to be equal to 7 with saturated sodium bicarbonate, and 20 mL of ethyl acetate were added, and the system was stirred for 10 minutes. The system was allowed to settle for layering, the organic phases were collected. The aqueous phase was extracted with ethyl acetate (30 mL×2), the organic phases were combined, and the aqueous phase was discarded. The organic phases were washed with 30 mL of saturated sodium chloride solution, and the system was allowed to settle for layering, the aqueous phase was discarded, and the organic phases were dried with an appropriate amount of anhydrous sodium sulfate. After drying, the desiccant was filtered out, and the filtrate was concentrated to dryness under reduced pressure to obtain a residue. The residue was passed through a flash column (an elution system was ethyl acetate/petroleum ether, and a ratio was gradually increased from 1:10 to 1:3), and an eluent of a corresponding product was collected and concentrated to dryness under reduced pressure to obtain compound XI-1 (5 g, 87.7%).

(5) tert-butyl (3-((allyloxy)methyl)-5-aminophenyl) carbamate (X-1)

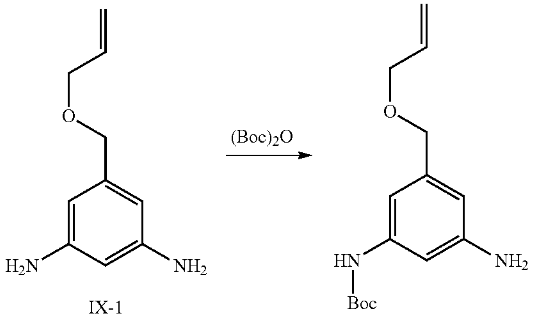

IX-1 X-1

| Reaction material | Feeding amount | Molecular weight | Mole number (mmol) | Eq |
|---|---|---|---|---|
| IX-1 | 5.0 g | 178.2 | 28.1 | 1 |
| $(Boc)_2O$ | 5.8 g | 218.3 | 26.7 | 0.95 |
| Tetrahydrofuran | 100 mL | — | — | — |

Compound IX-1 (5.0 g, 28.1 mmol) an tetrahydrofuran (50 mL) were added into a reaction flask, cooled to 0 °C., and then $(Boc)_2O$ (5.8 g, 26.7 mmol) was dissolved in tetrahydrofuran (50 mL) and added dropwise into the reaction system, and then the reaction was resumed at room temperature overnight. The reaction system was detected by TLC plate (PE/EA=2:1), and the raw materials disappeared under an ultraviolet analyzer at 254 nm, and the products no longer increased, so it was judged that the reaction was terminated. 100 mL of water and 30 mL of ethyl acetate were added, and the system was stirred for 10 minutes. The system was allowed to settle for layering, the organic phases were collected. The aqueous phase was extracted with ethyl acetate (30 mL×2), the organic phases were combined, and the aqueous phase was discarded. The organic phases were washed with 30 mL of saturated sodium chloride solution, and the system was allowed to settle for layering, the aqueous phase was discarded, and the organic phases were dried with an appropriate amount of anhydrous sodium sulfate. After drying, the desiccant was filtered out, and the filtrate was concentrated to dryness under reduced pressure to obtain a residue. The residue was passed through a flash column (an elution system was ethyl acetate/petroleum ether, and a ratio was gradually increased from 1:20 to 1:8), and an eluent of a corresponding product was collected and concentrated to dryness under reduced pressure to obtain compound X-1 (4.7 g, 60.3%).

(6) Synthesis of Macrocyclic Intermediate (XI-1)

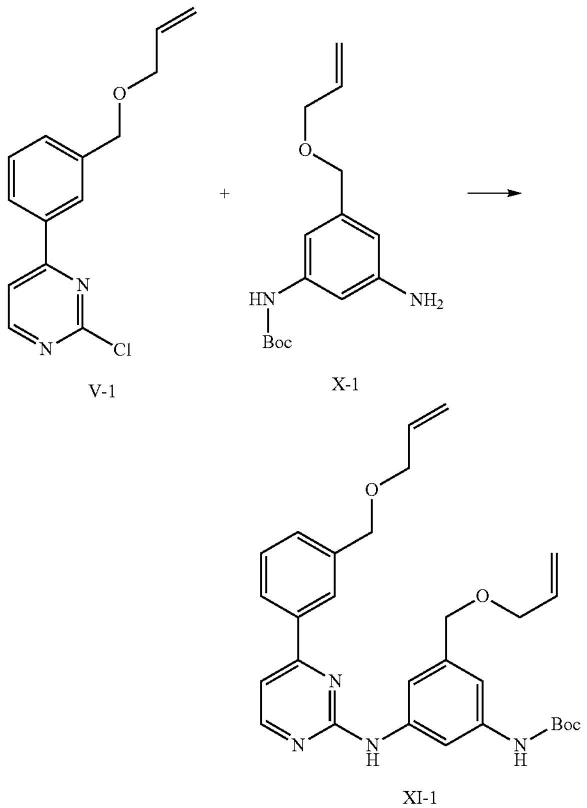

V-1 X-1 XI-1

| Reaction material | Feeding amount | Molecular weight | Mole number (mmol) | Eq |
|---|---|---|---|---|
| V-1 | 3.3 g | 260.7 | 12.6 | 1 |
| X-1 | 3.5 g | 278.3 | 12.6 | 1 |
| Cesium carbonate | 10.3 g | 325.8 | 31.5 | 2.5 |
| X-PHOS | 0.6 g | 476.7 | 1.3 | 0.1 |
| Tris(dibenzylideneacetone) dipalladium | 0.6 g | 915.7 | 0.6 | 0.05 |
| Dioxane | 55 mL | — | — | — |

Compound V-1 (3.3 g, 12.6 mmol), compound X-1 (3.5 g, 12.6 mmol), cesium carbonate (10.3 g, 31.5 mmol), X-PHOS (0.6 g, 0.6 mmol), tris(dibenzylideneacetone) dipalladium (0.6 g, 0.6 mmol) and dioxane (55 mL) were added into a reaction flask, heated to 100 °C, and reacted overnight. The reaction system was detected by TLC plate (PE/EA=3:1), and the raw materials disappeared under an ultraviolet analyzer at 254 nm, and the products no longer increased, so it was judged that the reaction was terminated. 30 mL of saturated ammonium chloride were added to quench the reaction, then 20 mL of ethyl acetate were added, and the system was stirred for 10 minutes. The system was allowed to settle for layering, the organic phases were collected. The aqueous phase was extracted with ethyl acetate (20 mL×2), the organic phases were combined, and the aqueous phase was discarded. The organic phases were washed with 20 mL of saturated sodium chloride solution, and the system was allowed to settle for layering, the aqueous phase was discarded, and the organic phases were dried with an appropriate amount of anhydrous sodium sulfate. After drying, the desiccant was filtered out, and the filtrate was concentrated to dryness under reduced pressure to obtain a residue. The residue was passed through a flash column (an elution system was ethyl acetate/petroleum ether, and a ratio was gradually increased from 1:20 to 1:5), and an eluent of a corresponding product was collected and concentrated to dryness under reduced pressure to obtain compound XI-1 (4.5 g, 71.4%).

(7) Synthesis of Macrocyclic Intermediate (XII-1)

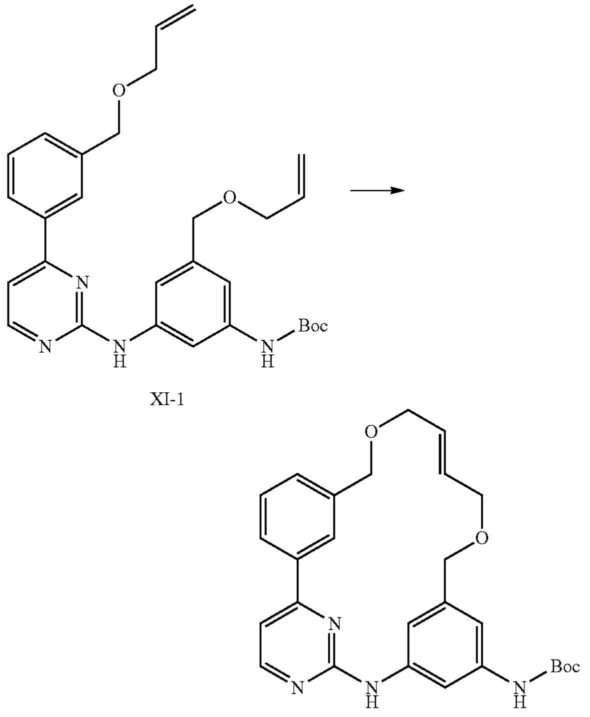

XI-1 XII-1

| Reaction material | Feeding amount | Molecular weight | Mole number (mmol) | Eq |
|---|---|---|---|---|
| Compound XI-1 | 4.5 g | 502.6 | 9.0 | 1 |
| Trifluoroacetic acid | 1.6 mL | — | — | — |
| Zhan Catalyst 1B | 0.7 g | — | 0.9 | 0.1 |
| Dichloromethane | 1350 mL | — | — | — |

Compound XI-1 (4.5 g, 9.0 mmol), trifluoroacetic acid (1.6 mL), Zhan Catalyst 1B (0.7 g, 0.9 mmol) and dichloromethane (1,350 mL) were added into a reaction flask, heated to 50 °C and reacted for 3 hours. The reaction system was detected by TLC plate (PE/EA=2:1), and the raw materials disappeared under an ultraviolet analyzer at 254 nm, and the products no longer increased, so it was judged that the reaction was terminated. The reaction solution was cooled to room temperature, and concentrated to dryness under reduced pressure to obtain a residue. The residue was passed through a flash column (an elution system was ethyl acetate/petroleum ether, and a ratio was gradually increased from 1:20 to 1:3), and an eluent of a corresponding product was collected and concentrated to dryness under reduced pressure to obtain compound XII-1 (2.1 g, 50%).

(8) Synthesis of Macrocyclic Intermediate (XIII-1)

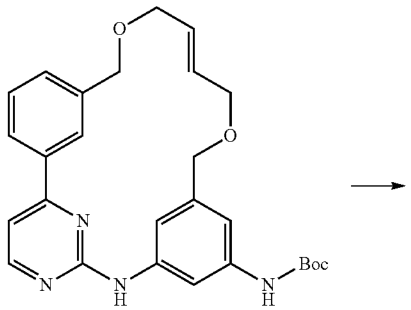

XII-1

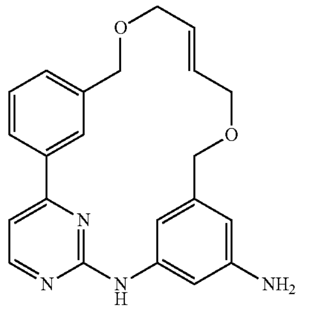

XIII-1

| Reaction material | Feeding amount | Molecular weight | Mole number (mmol) | Eq |
|---|---|---|---|---|
| XII-1 | 2.1 g | 474.6 | 4.4 | 1 |
| EA/HCl | 20 mL | — | — | — |

Compound XII-1 (2.1 g, 4.4 mmol) and EA/HCl (20 mL) were added into a reaction flask, and then reacted at room temperature for 1 hour. The reaction system was detected by TLC plate (PE/EA=2:1), and the raw materials disappeared under an ultraviolet analyzer at 254 nm, and the products no longer increased, so it was judged that the reaction was terminated. The system was directly concentrated to dryness under reduced pressure to obtain a residue. The residue was added into water, and then the pH was adjusted to be equal to 8 with saturated sodium bicarbonate. Solids were precipitated, and filtered, and then the filter cake was washed twice with water, and dried to obtain a crude product. The crude product was passed through a flash column (an elution system was methanol/dichloromethane, and a ratio was gradually increased from 1:100 to 1:30), and an eluent of a corresponding product was collected and concentrated to dryness under reduced pressure to obtain compound XIII-1 (1.6 g, 97%). MS (m/z): 375 $(MH)^+$. $^1H$ NMR (400 MHz, DMSO_d6) δ 4.00-4.06 (m, 4H), 4.35 (s, 2H), 4.52 (s, 2H), 5.01 (s, 2H), 5.77-5.81 (m, 2H), 6.30 (s, 1H), 6.35 (s, 1H), 7.40-7.42 (d, 1H), 7.53-7.54 (d, 2H), 7.84 (s, 1H), 8.02-8.04 (d, 1H), 8.28 (s, 1H), 8.51-8.53 (d, 1H), 9.47 (s, 1H).

(9) Synthesis of Macrocyclic Intermediate (XVI-1)

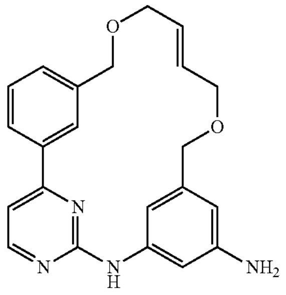

XIII-1

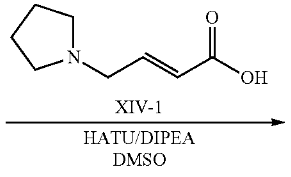

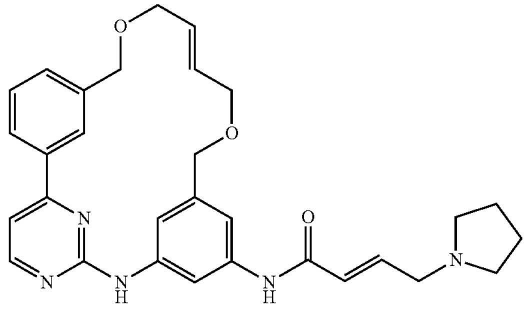

XVI-1

| Reaction material | Feeding amount | Molecular weight | Mole number (mmol) | Eq |
|---|---|---|---|---|
| XIII-1 | 500.0 mg | 374.4 | 1.3 | 1 |
| XIV-1 | 248.3 mg | 155.2 | 1.6 | 1.2 |
| HATU | 760.4 mg | 380.2 | 2.0 | 1.5 |
| N,N-diisopropylethylamine | 335.9 mg | 129.2 | 2.6 | 2 |
| Dimethyl sulfoxide | 6 mL | — | — | — |

Compound XIII-1 (500.0 mg, 1.3 mmol), compound XIV-1 (248.3 mg, 1.6 mmol), HATU (760.4 mg, 2.0 mmol) and dimethyl sulfoxide (6 mL) were added into a reaction flask, then cooled to 5 °C, and then N,N-diisopropylethylamine (335.9 g, 2.6 mmol) was added dropwise into the system, and reacted at room temperature overnight under the protection of nitrogen. The reaction system was detected by LC-MS, and the raw materials disappeared, and the products no longer increased, so it was judged that the reaction was terminated. Ice water was added into the system and solids were precipitated, the system was filtered, and then the filter cake was washed twice with water, and dried to obtain a crude product. The crude product was prepared into compound XIV-1 (102 mg, purity 98% by HPLC) by preparing a liquid phase (Xbridge C18, 5 μm 19×150 mm/water-acetonitrile/35-70-8 min-300 m). MS (m/z): 512 $(MH)^+$. $^1H$ NMR (400 MHz, DMSO_d6) δ 1.72-1.75 (d, 4H), 2.48 (s, 4H), 3.23-3.24 (d, 2H), 4.01-4.10 (m, 4H), 4.47-4.54 (d, 4H), 5.74-5.85 (m, 2H), 6.30-6.34 (d, 1H), 6.75-6.81 (m, 1H), 7.36 (s, 1H), 7.45-7.48 (m, 2H), 7.52-7.57 (m, 2H), 8.04-8.06 (d, 1H), 8.26-8.32 (d, 2H), 8.56-8.57 (d, 1H), 9.82 (s, 1H), 10.04 (s, 1H).

(10) Synthesis of Macrocyclic Intermediate (XVII-1)

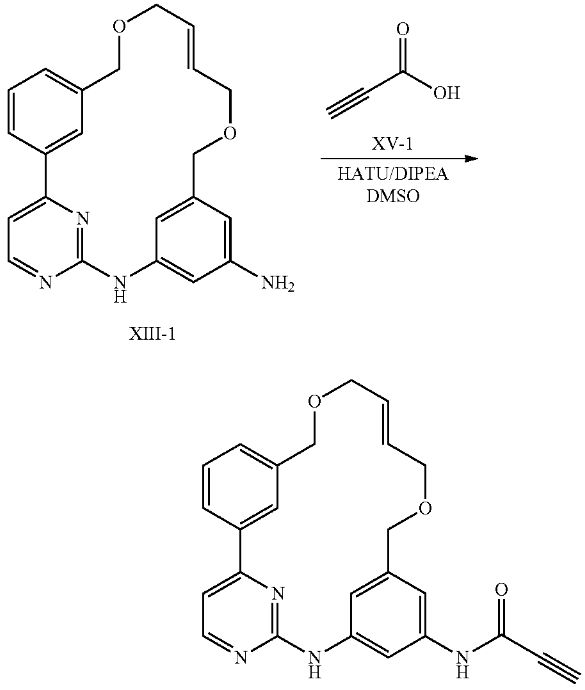

XIII-1

XVII-1

| Reaction material | Feeding amount | Molecular weight | Mole number (mmol) | Eq |
|---|---|---|---|---|
| XIII-1 | 500.0 mg | 374.4 | 1.3 | 1 |
| XV-1 | 112.0 mg | 70.0 | 1.6 | 1.2 |
| HATU | 760.4 mg | 380.2 | 2.0 | 1.5 |
| N,N-diisopropylethylamine | 335.9 mg | 129.2 | 2.6 | 2 |
| Dimethyl sulfoxide | 6 mL | — | — | — |

Compound XIII-1 (500.0 mg, 1.3 mmol), XV-1 (112.0 mg, 1.6 mmol), HATU (760.4 mg, 2.0 mmol) and dimethyl sulfoxide (6 mL) were added into a reaction flask, then cooled to 5 °C, and then N,N-diisopropylethylamine (335.9 g, 2.6 mmol) was added dropwise into the system, and reacted at room temperature overnight under the protection of nitrogen. The reaction system was detected by LC-MS, and the raw materials disappeared, and the products no longer increased, so it was judged that the reaction was terminated. Ice water was added into the system and solids were precipitated, the system was filtered, and then the filter cake was washed twice with water, and dried to obtain a crude product. The crude product was prepared into compound XVII-1 (110 mg) by preparing a liquid phase (Xbridge C18, 5 μm 19×150 mm/water+acetonitrile/35-70-8 min-300 m). MS (m/z): 427 $(MH)^+$. $^1H$ NMR (400 MHz, DMSO_d6) δ 4.01-4.09 (m, 4H), 4.40 (s, 1H), 4.46-4.53 (d, 4H), 5.76-5.81 (m, 2H), 7.25 (s, 1H), 7.43-7.48 (m, 2H), 7.54-7.56 (d, 2H), 8.04-8.06 (d, 1H), 8.25 (s, 1H), 8.37 (s, 1H), 8.56-8.57 (d, 1H), 9.84 (s, 1H), 10.81 (s, 1H).

Other Examples

The compounds in Table 1 were all synthesized according to the above synthesis route by selecting suitable starting materials and suitable reaction reagents.

TABLE 1

Compounds with general structural formula (I) and general structural formula (II) that can be synthesized by the method of the present invention

| Serial Number | Number | Structure | m/z $(MH)^+$ |
|---|---|---|---|
| 1 | XIII-1 | 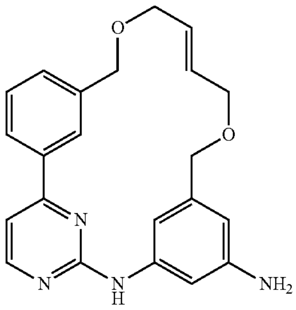 | 375.14 |

TABLE 1-continued
| Compounds with general structural formula (I) and general structural formula (II) that can be synthesized by the method of the present invention | | | |
|---|---|---|---|
| Serial Number | Number | Structure | m/z (MH)+ |
| 2 | XIII-2 | 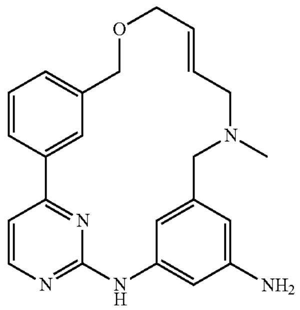 | 388.21 |
| 3 | XVI-1 | 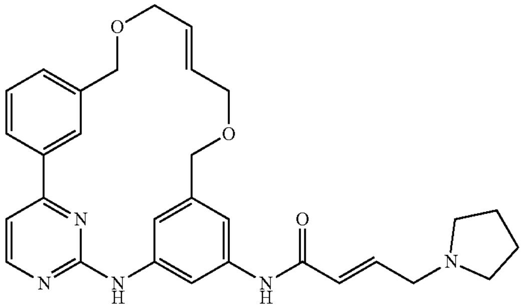 | 512.26 |
| 4 | XVI-2 | 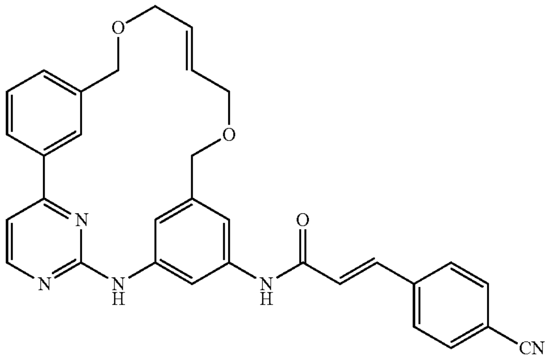 | 530.21 |
| 5 | XVI-3 | 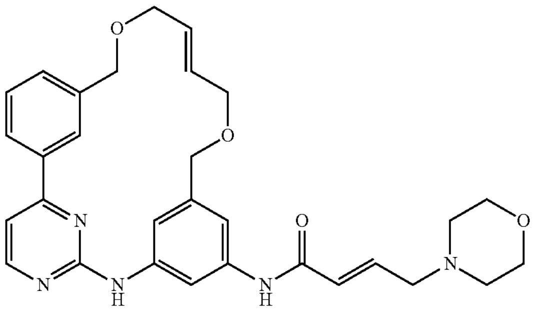 | 528.25 |

TABLE 1-continued
Compounds with general structural formula (I) and general structural formula (II) that can be synthesized by the method of the present invention
| Serial Number | Number | Structure | m/z (MH)+ |
|---|---|---|---|
| 6 | XVI-4 | 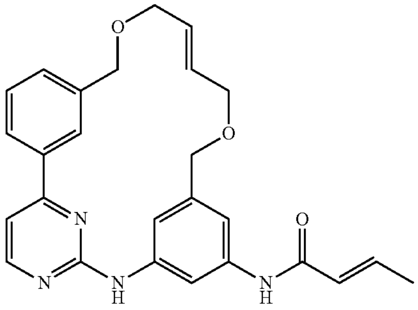 | 443.20 |
| 7 | XVI-5 | 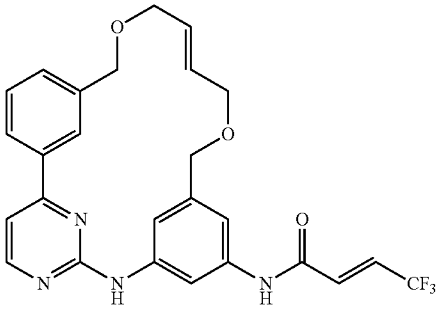 | 497.17 |
| 8 | XVI-6 | 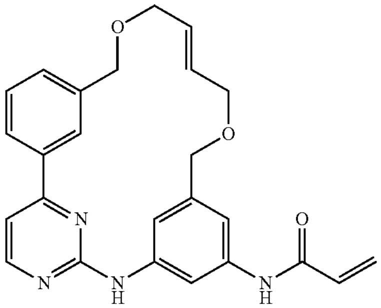 | 429.18 |
| 9 | XVI-7 | 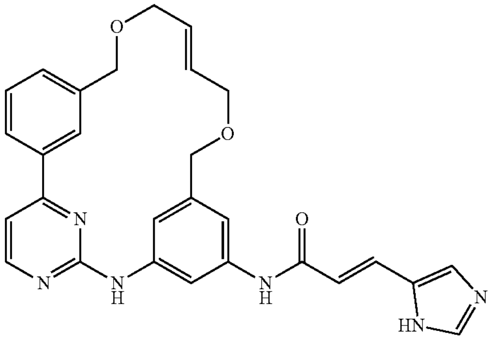 [SMILES: O=C(/C=C/c1cnc[nH]1)Nc1cc2cc(c1)Nc1nccc(n1)-c1cccc(c1)COC/C=C/COC2] | 495.21 |

TABLE 1-continued
Compounds with general structural formula (I) and general structural formula (II) that can be synthesized by the method of the present invention
| Serial Number | Number | Structure | m/z (MH)+ |
|---|---|---|---|
| 10 | XVI-8 | 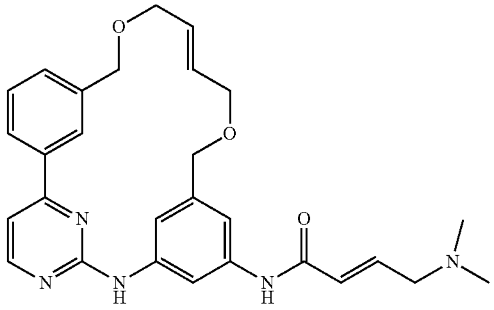 [SMILES: CN(C)C/C=C/C(=O)Nc1cc2cc(c1)Nc1nccc(n1)-c1cccc(c1)COC/C=C/COC2] | 486.24 |
| 11 | XVI-9 | 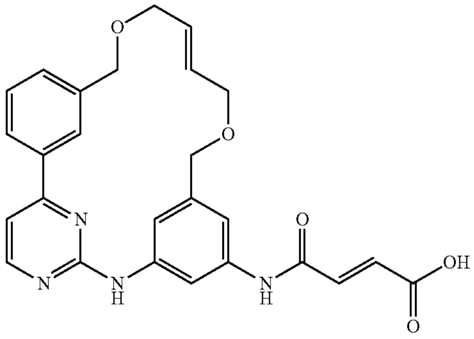 [SMILES: O=C(O)/C=C/C(=O)Nc1cc2cc(c1)Nc1nccc(n1)-c1cccc(c1)COC/C=C/COC2] | 473.17 |
| 12 | XVI-10 | 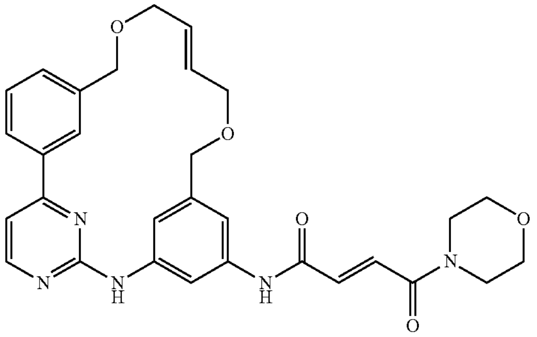 [SMILES: O=C(/C=C/C(=O)N1CCOCC1)Nc1cc2cc(c1)Nc1nccc(n1)-c1cccc(c1)COC/C=C/COC2] | 542.23 |
| 13 | XVI-11 | 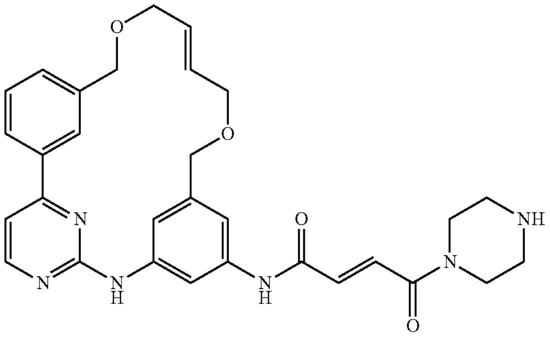 [SMILES: O=C(/C=C/C(=O)N1CCNCC1)Nc1cc2cc(c1)Nc1nccc(n1)-c1cccc(c1)COC/C=C/COC2] | 541.25 |

TABLE 1-continued
Compounds with general structural formula (I) and general structural formula (II) that can be synthesized by the method of the present invention
| Serial Number | Number | Structure | m/z (MH)+ |
|---|---|---|---|
| 14 | XVI-12 | 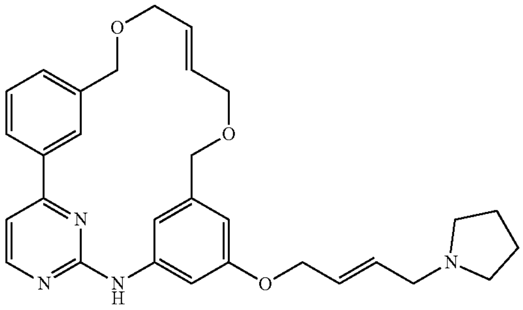 [SMILES: C1=C/COCc2cccc(c2)-c2ccnc(n2)Nc2cc(cc(OC/C=C/CN3CCCC3)c2)COC/1] | 499.26 |
| 15 | XVI-13 | 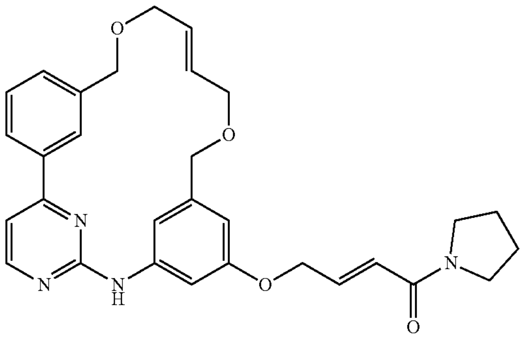 [SMILES: O=C(/C=C/COc1cc2cc(c1)Nc1nccc(n1)-c1cccc(c1)COC/C=C/COC2)N1CCCC1] | 513.24 |
| 16 | XVI-14 | 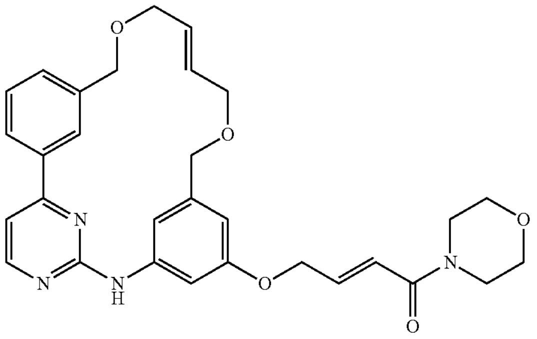 [SMILES: O=C(/C=C/COc1cc2cc(c1)Nc1nccc(n1)-c1cccc(c1)COC/C=C/COC2)N1CCOCC1] | 529.24 |
| 17 | XVI-15 | 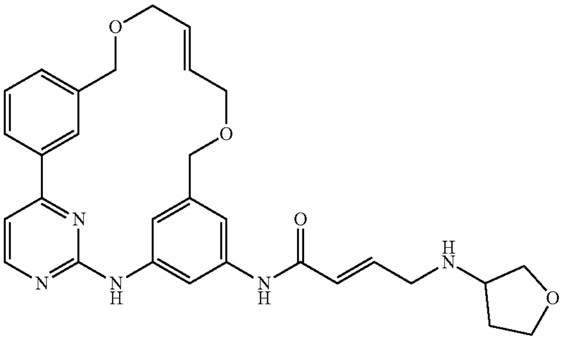 | 526.27 |

TABLE 1-continued
Compounds with general structural formula (I) and general structural formula (II) that can be synthesized by the method of the present invention
| Serial Number | Number | Structure | m/z $(MH)^+$ |
|---|---|---|---|
| 18 | XVI-16 | 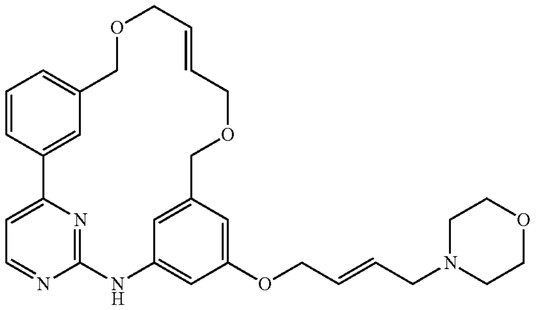 [SMILES: C1=C/COCc2cccc(c2)-c2ccnc(n2)Nc2cc(cc(OC/C=C/CN3CCOCC3)c2)COC/1] | 515.26 |
| 19 | XVI-17 | 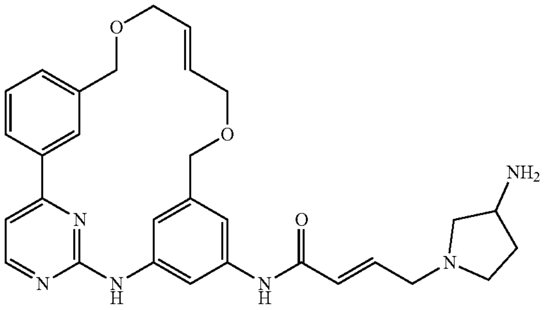 [SMILES: NC1CCN(C/C=C/C(=O)Nc2cc3cc(c2)Nc2nccc(n2)-c2cccc(c2)COC/C=C/COC3)C1] | 527.27 |
| 20 | XVI-18 | 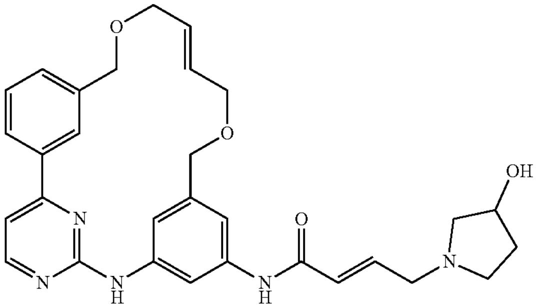 [SMILES: O=C(/C=C/CN1CCC(O)C1)Nc1cc2cc(c1)Nc1nccc(n1)-c1cccc(c1)COC/C=C/COC2] | 527.25 |
| 21 | XVI-19 | 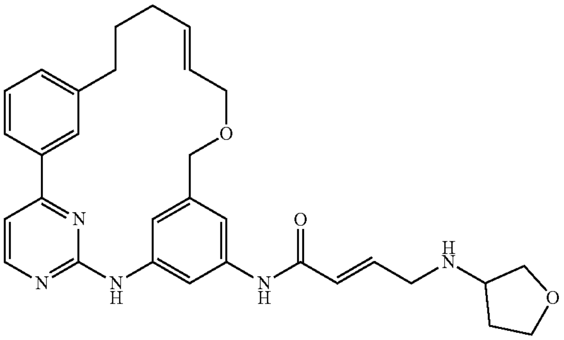 | 528.25 |

TABLE 1-continued
| Compounds with general structural formula (I) and general structural formula (II) that can be synthesized by the method of the present invention | | | |
|---|---|---|---|
| Serial Number | Number | Structure | m/z (MH)$^+$ |
| 22 | XVI-20 | 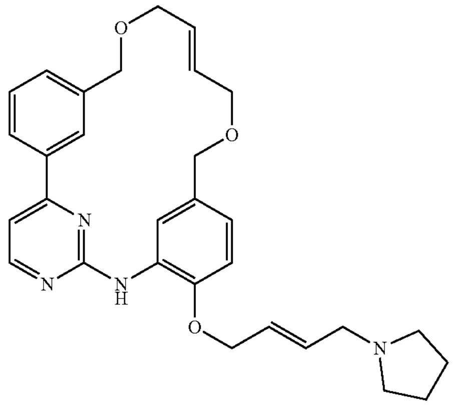 [SMILES: C1=C/COCc2ccc(OC/C=C/CN3CCCC3)c(c2)Nc2nccc(n2)-c2cccc(c2)COC/1] | 499.26 |
| 23 | XVI-21 | 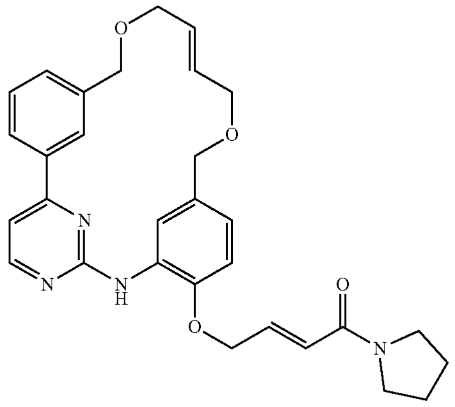 [SMILES: O=C(/C=C/COc1ccc2cc1Nc1nccc(n1)-c1cccc(c1)COC/C=C/COC2)N1CCCC1] | 513.24 |
| 24 | XVI-22 | 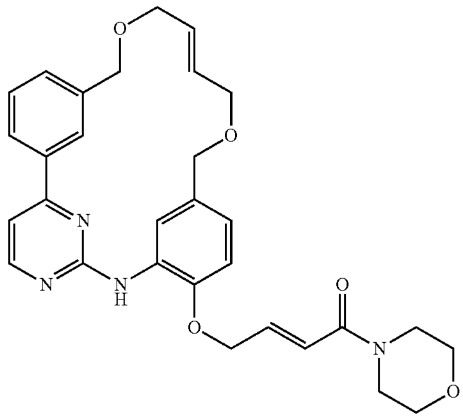 [SMILES: O=C(/C=C/COc1ccc2cc1Nc1nccc(n1)-c1cccc(c1)COC/C=C/COC2)N1CCOCC1] | 529.24 |

TABLE 1-continued
| Serial Number | Number | Structure | m/z (MH)+ |
|---|---|---|---|
| 25 | XVI-23 | 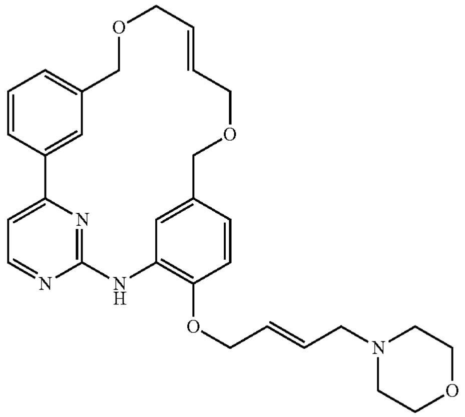 [SMILES: C1=C/COCc2ccc(OC/C=C/CN3CCOCC3)c(c2)Nc2nccc(n2)-c2cccc(c2)COC/1] | 515.26 |
| 26 | XVI-24 | 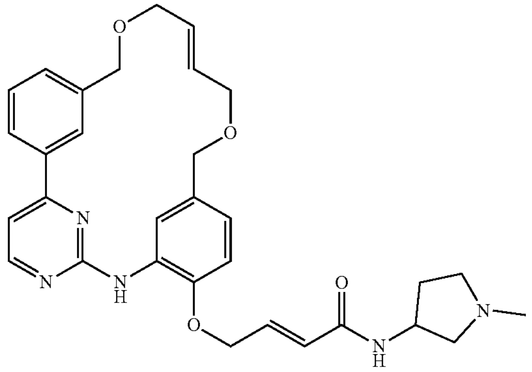 [SMILES: CN1CCC(NC(=O)/C=C/COc2ccc3cc2Nc2nccc(n2)-c2cccc(c2)COC/C=C/COC3)C1] | 542.27 |
| 27 | XVI-25 | 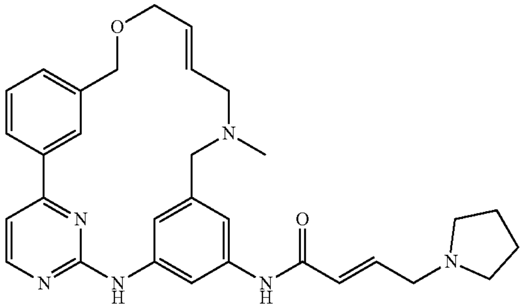 [SMILES: CN1C/C=C/COCc2cccc(c2)-c2ccnc(n2)Nc2cc(cc(NC(=O)/C=C/CN3CCCC3)c2)C1] | 525.29 |
| 28 | XVI-26 | 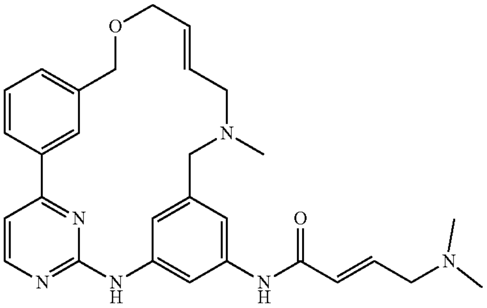 [SMILES: CN(C)C/C=C/C(=O)Nc1cc2cc(c1)Nc1nccc(n1)-c1cccc(c1)COC/C=C/CN(C)C2] | 499.27 |
Compounds with general structural formula (I) and general structural formula (II) that can be synthesized by the method of the present invention TABLE 1-continued
Compounds with general structural formula (I) and general structural formula (II) that can be synthesized by the method of the present invention
| Serial Number | Number | Structure | m/z (MH)$^+$ |
|---|---|---|---|
| 29 | XVI-27 | 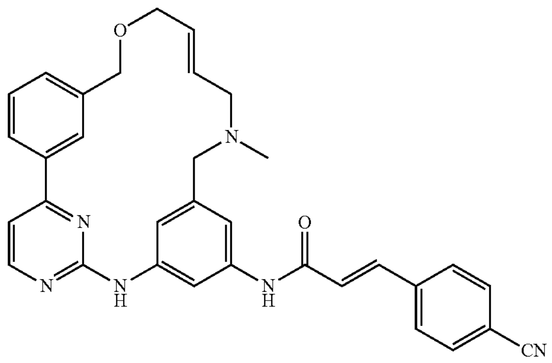 [SMILES: CN1C/C=C/COCc2cccc(c2)-c2ccnc(n2)Nc2cc(cc(NC(=O)/C=C/c3ccc(C#N)cc3)c2)C1] | 543.24 |
| 30 | XVI-28 | 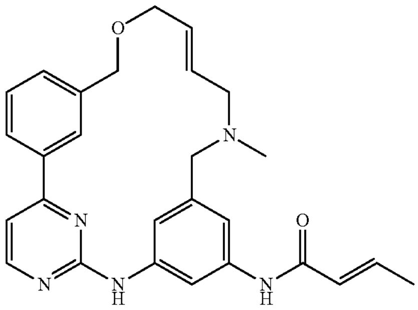 [SMILES: C/C=C/C(=O)Nc1cc2cc(c1)Nc1nccc(n1)-c1cccc(c1)COC/C=C/CN(C)C2] | 456.23 |
| 31 | XVI-29 | 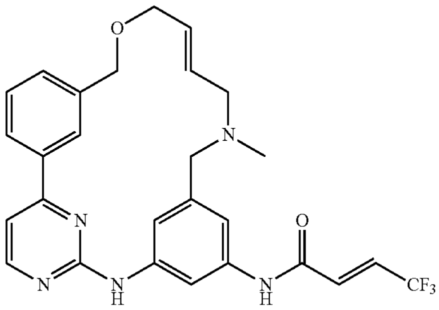 [SMILES: CN1C/C=C/COCc2cccc(c2)-c2ccnc(n2)Nc2cc(cc(NC(=O)/C=C/C(F)(F)F)c2)C1] | 510.20 |
| 32 | XVI-30 | 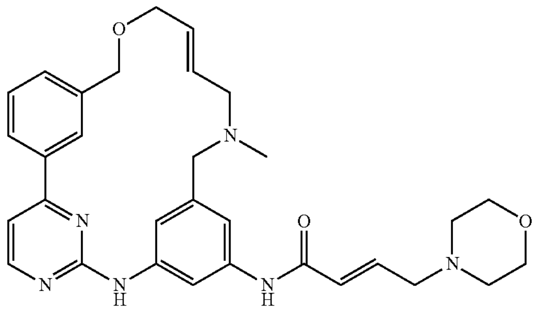 [SMILES: CN1C/C=C/COCc2cccc(c2)-c2ccnc(n2)Nc2cc(cc(NC(=O)/C=C/CN3CCOCC3)c2)C1] | 541.28 |

TABLE 1-continued
Compounds with general structural formula (I) and general structural formula (II) that can be synthesized by the method of the present invention
| Serial Number | Number | Structure | m/z (MH)+ |
|---|---|---|---|
| 33 | XVI-31 | 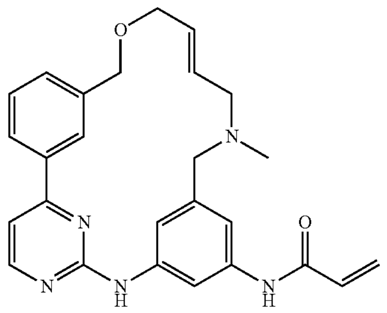 [SMILES: C=CC(=O)Nc1cc2cc(c1)Nc1nccc(n1)-c1cccc(c1)COC/C=C/CN(C)C2] | 442.22 |
| 34 | XVI-32 | 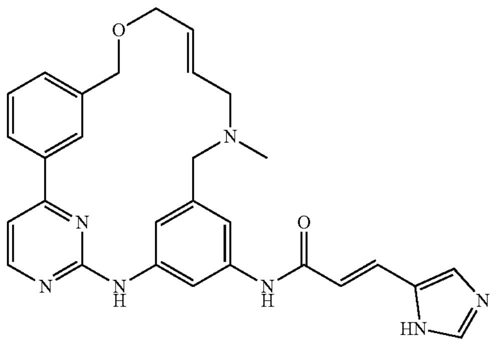 [SMILES: CN1C/C=C/COCc2cccc(c2)-c2ccnc(n2)Nc2cc(cc(NC(=O)/C=C/c3cnc[nH]3)c2)C1] | 508.24 |
| 35 | XVI-33 | 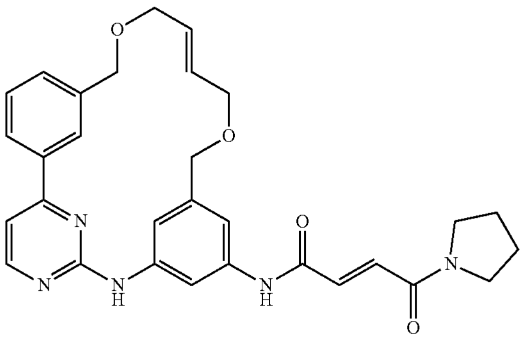 [SMILES: O=C(/C=C/C(=O)N1CCCC1)Nc1cc2cc(c1)Nc1nccc(n1)-c1cccc(c1)COC/C=C/COC2] | 526.24 |
| 36 | XVI-34 | 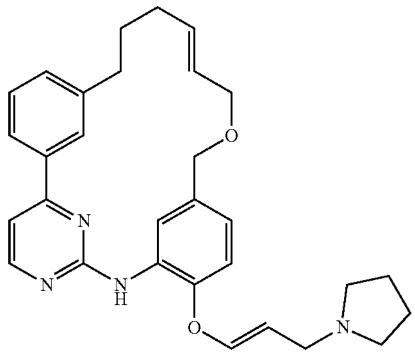 [SMILES: C1=C/COCc2ccc(O/C=C/CN3CCCC3)c(c2)Nc2nccc(n2)-c2cccc(c2)CCC/1] | 485.25 |

TABLE 1-continued
| Serial Number | Number | Structure | m/z (MH)+ |
|---|---|---|---|
| | | Compounds with general structural formula (I) and general structural formula (II) that can be synthesized by the method of the present invention | |
| 37 | XVII-1 | 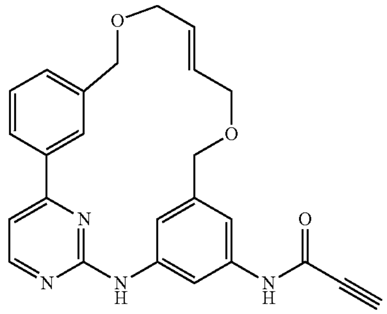 [SMILES: C#CC(=O)Nc1cc2cc(c1)Nc1nccc(n1)-c1cccc(c1)COC/C=C/COC2] | 427.17 |
| 38 | XVII-2 | 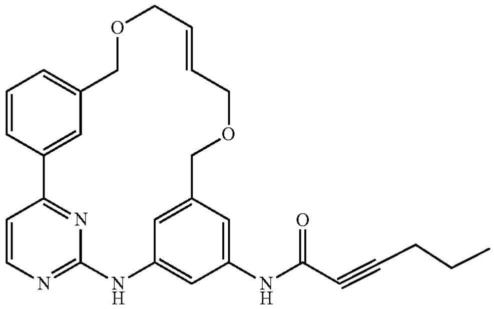 [SMILES: CCCC#CC(=O)Nc1cc2cc(c1)Nc1nccc(n1)-c1cccc(c1)COC/C=C/COC2] | 469.22 |
| 39 | XVII-3 | 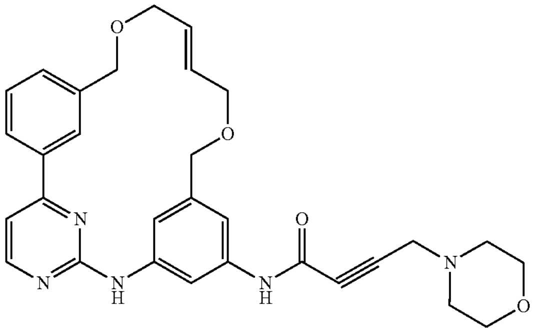 [SMILES: O=C(C#CCN1CCOCC1)Nc1cc2cc(c1)Nc1nccc(n1)-c1cccc(c1)COC/C=C/COC2] | 525.24 |
| 40 | XVII-4 | 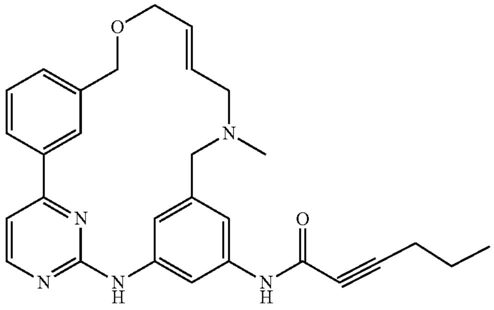 [SMILES: CCCC#CC(=O)Nc1cc2cc(c1)Nc1nccc(n1)-c1cccc(c1)COC/C=C/CN(C)C2] | 482.25 |

TABLE 1-continued

| Compounds with general structural formula (I) and general structural formula (II) that can be synthesized by the method of the present invention | | | |
|---|---|---|---|
| Serial Number | Number | Structure | m/z (MH)+ |
| 41 | XVII-5 | 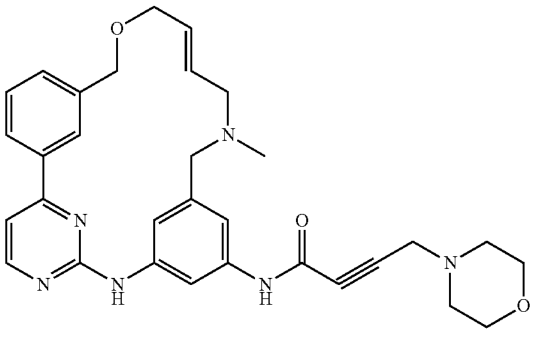 [SMILES: CN1C/C=C/COCc2cccc(c2)-c2ccnc(n2)Nc2cc(cc(NC(=O)C#CCN3CCOCC3)c2)C1] | 539.27 |

Pharmacological Test

The biological efficacy of the compounds of the present invention can be evaluated through an enzyme inhibitory activity, a cell proliferation inhibitory activity and other aspects. Methods for determining the enzyme inhibitory activity, the cell proliferation inhibitory activity and the like of the compounds comprise, but are not limited to, the following methods.

Method for Determining Enzyme Inhibitory Activity

An activity to a human recombinant protein kinase of a series of compounds was determined by a radioisotope labeling method, which was provided by Eurofins Company. A compound to be detected was mixed with a corresponding protein kinase buffer (20 mM propyl sulfonate (MOPS, pH17.), 1 mM EDTA, 0.10 β-mercaptoethanol, 0.010 Brij-35, 54 glycerol, and 1 mg/mL BSA), the mixture was added into a reaction system (100 μM reaction substrate KKRNRTLTV, 8 mM MOPS with a pH value of 7.0, 10 mM MgAcetate, 0.2 mM EDTA, and a certain concentration of γ-$^{33}$P-ATP). After adding an MgATP composite solution, the reaction was started at room temperature for 40 minutes, and the reaction was terminated by adding 5 μl of 31 phosphoric acid solution. Then, 10 μl of reaction solution was dropwise added onto a filter and washed with 75 mM phosphoric acid solution for three times, 5 minutes each time, then washed with methanol once again, and dried and subjected to scintillation counting.

Table 2 shows inhibitory activity per unit concentration (1 μM). Table 3 shows $XC_{50}$ of some compounds.

TABLE 2

Inhibitory activity per unit concentration (1 μM)

| Inhibitory activity per unit concentration/Activity % | Ab1 (h) | ALK1 (h) | ALK2 (h) | BTK (h) | cSRC (h) | Flt3 (D835Y) (h) | Flt3 (h) | JAK1 (h) | JAK2 (h) | JAK3 (h) |
|---|---|---|---|---|---|---|---|---|---|---|
| XIII-1 | 11 | 4 | 2 | 6 | 3 | −1 | 4 | 3 | 4 | 10 |
| XIII-2 | 57 | 17 | 13 | 71 | 38 | 1 | 7 | 4 | 18 | 77 |
| XVI-1 | −1 | 0 | −3 | 2 | 1 | −1 | 1 | 7 | 1 | 9 |
| XVI-2 | 42 | 28 | 55 | 61 | 61 | 3 | 12 | 52 | 25 | 56 |
| XVI-3 | 8 | 3 | 2 | 7 | 1 | 1 | 3 | 7 | 0 | 8 |
| XVI-4 | 11 | 4 | 6 | 9 | 4 | −1 | 5 | 9 | 2 | 11 |
| XVI-5 | 57 | 16 | 72 | 88 | 56 | 7 | 17 | 27 | 23 | 75 |
| XVI-6 | 17 | 5 | 11 | 16 | 8 | −1 | 5 | 11 | 1 | 16 |
| XVI-7 | 17 | 6 | 23 | 45 | 18 | −1 | 7 | 27 | 2 | 21 |
| XVI-8 | 4 | 1 | −3 | 9 | 5 | −2 | 2 | 15 | 3 | 19 |
| XVI-9 | 45 | — | 19 | 62 | 15 | 1 | 4 | 2 | −2 | 4 |
| XVI-10 | 9 | — | 4 | 31 | 14 | 5 | 3 | 5 | −2 | 2 |
| XVI-11 | −1 | — | 3 | 18 | 10 | 1 | 1 | 9 | 1 | 6 |
| XVI-12 | 3 | — | 1 | 38 | 13 | 7 | −8 | 39 | 15 | 26 |
| XVI-13 | 39 | — | 11 | 49 | 24 | −2 | 24 | 52 | 18 | 34 |
| XVI-14 | 46 | — | 8 | 47 | 21 | 3 | 8 | 31 | 8 | 21 |
| XVI-15 | 7 | — | −1 | 12 | 15 | 6 | 20 | 28 | 9 | 6 |
| XVI-16 | 19 | — | 2 | 48 | 25 | −1 | 20 | 41 | 13 | 32 |
| XVI-17 | −4 | — | 1 | 17 | 8 | 8 | 16 | 16 | 2 | 4 |
| XVI-18 | 2 | — | −1 | 17 | 14 | 4 | 19 | 23 | 9 | 8 |
| XVI-19 | 2 | — | 0 | 17 | 16 | −3 | 23 | 19 | 6 | 6 |
| XVI-20 | 85 | — | 61 | 90 | 94 | 33 | 91 | 98 | 90 | 97 |
| XVI-21 | 92 | — | 92 | 78 | 96 | 44 | 82 | 103 | 80 | 95 |
| XVI-22 | 81 | — | 91 | 82 | 92 | 41 | 96 | 94 | 103 | 100 |
| XVI-23 | 85 | — | 79 | 90 | 98 | 27 | 78 | 90 | 92 | 10 |
| XVI-24 | 81 | — | 83 | 86 | 94 | 50 | 82 | 107 | 87 | 88 |
| XVI-25 | 35 | 13 | 1 | 64 | 34 | 0 | 6 | 28 | 29 | 83 |
| XVI-26 | 32 | 9 | 0 | 50 | 27 | 0 | 7 | 9 | 20 | 74 |
| XVI-27 | 45 | 21 | 32 | 77 | 40 | 2 | 8 | 22 | 39 | 52 |

TABLE 2-continued

| Inhibitory activity per unit concentration (1 μM) | | | | | | | | | | |
|---|---|---|---|---|---|---|---|---|---|---|
| Inhibitory activity per unit concentration/Activity % | Ab1 (h) | ALK1 (h) | ALK2 (h) | BTK (h) | cSRC (h) | Flt3 (D835Y) (h) | Flt3 (h) | JAK1 (h) | JAK2 (h) | JAK3 (h) |
| XVI-28 | 37 | 11 | 13 | 57 | 14 | 1 | 8 | 5 | 11 | 51 |
| XVI-29 | 60 | 25 | 19 | 78 | 38 | 3 | 10 | 9 | 17 | 36 |
| XVI-30 | 55 | 17 | 9 | 66 | 21 | 2 | 7 | 9 | 16 | 61 |
| XVI-31 | 50 | 19 | 15 | 86 | 25 | 2 | 7 | 6 | 15 | 57 |
| XVI-32 | 50 | 16 | 21 | 82 | 28 | 0 | 5 | 9 | 15 | 30 |
| XVI-33 | 38 | — | 12 | 86 | 56 | 10 | 2 | 19 | 2 | 17 |
| XVI-34 | 98 | — | 81 | 87 | 87 | 79 | 125 | 90 | 101 | 87 |
| XVII-1 | 1 | 6 | 6 | 8 | 8 | −1 | 4 | 3 | 1 | 16 |
| XVII-2 | 13 | 12 | 12 | 36 | 21 | −1 | 5 | 12 | 3 | 36 |
| XVII-4 | 52 | 23 | 27 | 80 | 49 | 3 | 7 | 8 | 23 | 83 |
| XVII-3 | 8 | 3 | 3 | 17 | 5 | 0 | 2 | 4 | 1 | 14 |
| XVII-5 | 45 | 12 | 10 | 72 | 28 | 1 | 4 | 3 | 15 | 60 |

TABLE 3

| $IC_{50}$ of some compounds | | | | | | | | | | | | |
|---|---|---|---|---|---|---|---|---|---|---|---|---|
| Kinase/ compound $IC_{50}$ (nM) | Ab1 (h) | BTK (h) | EGFR (T790M, L858R) (h) | Flt3 (D835Y) (h) | Flt3 (h) | JAK1 (h) | JAK2 (h) | JAK3 (h) | KDR (h) | Ret (h) | Ret (V804M) (h) | TrkA (h) |
| XIII-1 | — | 157 | 19 | 9 | 8 | 17 | 6 | — | 50 | 123 | — | 2 |
| XVI-1 | — | 29 | 10 | 3 | 2 | 69 | 9 | — | 17 | 66 | — | 1 |
| XVI-3 | — | 40 | 21 | 5 | 4 | 44 | 6 | — | 21 | 145 | — | 2 |
| XVI-4 | — | 238 | 60 | 10 | 5 | 44 | 10 | — | 15 | 314 | — | 2 |
| XVI-6 | — | 348 | 64 | 10 | 15 | 106 | 16 | — | 61 | 202 | — | 2 |
| XVI-8 | — | 48 | 17 | 9 | 9 | 262 | 29 | — | 97 | 79 | — | 3 |
| XVI-9 | 973 | — | — | 5 | 31 | 19 | 7 | 17 | 46 | — | — | 3 |
| XVI-10 | 139 | — | — | 4 | 21 | 89 | 17 | 44 | 40 | — | — | 16 |
| XVI-11 | 34 | — | — | 6 | 22 | 167 | 38 | 151 | 189 | — | — | 21 |
| XVI-12 | 111 | — | — | 3 | 15 | 492 | 124 | — | — | — | 122 | 18 |
| XVI-28 | — | 1471 | 300 | 20 | 9 | 40 | 86 | — | 76 | 1980 | — | 20 |
| XVI-26 | — | 1247 | 164 | 17 | 21 | 136 | 328 | — | 329 | 594 | — | 28 |
| XVII-1 | — | 00 | 39 | 7 | 7 | 33 | 13 | — | 32 | 110 | — | 2 |

Cell Proliferation Inhibitory Activity:

Human cancer cells were purchased from ATCC. The cells were cultured in a culture medium according to the work instruction of ATCC. A dose-response curve was drawn by XL-fitting to determine an $IC_{50}$ value of a compound. The $IC_{50}$ was defined as a concentration of the compound required to inhibit growth of 50% cells. As shown in the following table, the compounds of the present invention inhibited cell proliferation. Data showed that the compounds of the present invention had an inhibitory activity to growth of tumor cells. Cell proliferation inhibition could be detected by a MTT method (3-(4,5-Dimethylthiazol-2-yl)-2,5-diphenyltetrazolium bromide, and MTT; and 3-(4,5-dimethyl thiazole-2)-2,5-diphenyltertazolium bromide, and thiazolyl blue).

The cells were cultured in a culture dish first, and the cells in a logarithmic growth phase were inoculated into a 96-well plate (3,000 to 5,000 adherent cells/well, 10,000 to 30,000 suspended cells/well) according to a specific number, with 100 microliters per well, and then cultured in an incubator of 5% $CO_2$ and 37 °C. After standing overnight, 100 microliters of drugs with different concentration gradients prepared by a specified culture medium were added, each concentration gradient was provided with triple wells to ensure the accuracy of results, and a blank control group and a solvent control group were provided. After adding the drugs, the cells were cultured in the incubator for 72 hours. A MTT testing solution (5 mg/ml MTT solution dissolved in normal saline, stored in the dark at 4 °C) was prepared in advance on the day of MTT experiment, 20 μl of MTT solution was added into each well, and then the cells were continuously cultured in the incubator for 2 hours to 4 hours. Then, 50 μl of 20% SDS solution was added into each well to stand overnight, and then an absorbance at 570 nm was detected by a microplate reader to calculate an in-vitro proliferation inhibition rate to tumor cells of the drugs. An absorbance of a general control group should be a normal value between 0.8 and 1.2. After obtaining absorbance data, a change curve of an inhibition rate was fitted by GraphPad Prism6.03 software and an $IC_{50}$ value was calculated.

Calculation of drug inhibition rate: relative cell proliferation inhibition rate=[(control group A570−experimental group A570)/control group A570×10000, wherein A570 represented the absorbance at 570 nm.

TABLE 4

| Summary of MTT research results of compounds of the present invention to 8 cell models | | | |
|---|---|---|---|
| | | $IC_{50}$ (μM) | |
| Cell species | Cell type | XVI-3 | XVI-1 |
| HGC-27 | Human gastric cancer cells | 0.495 | 0.110 |
| MGC-803 | Human gastric cancer cells | 2.764 | 0.573 |
| HL-60 | Human acute myelogenous leukemia | 0.866 | 0.326 |
| K562 | Human acute myelogenous leukemia | 2.884 | 0.470 |
| MV4-11 | Human acute myelogenous leukemia | 0.087 | 0.030 |

TABLE 4-continued

Summary of MTT research results of compounds of the present invention to 8 cell models

| Cell species | Cell type | IC50 (μM) | |
|---|---|---|---|
| | | XVI-3 | XVI-1 |
| MM1S | Human myeloma cells | 0.379 | 0.092 |
| U266 | Human myeloma cells | 2.699 | 0.614 |
| RPMI 8226 | Human myeloma cells | 2.039 | 0.463 |
| Karpas-299 | Human anaplastic large cell lymphoma cells | 1.183 | 0.133 |
| TT | Human medullary thyroid cancer | 1.470 | 0.143 |
| HT1080 | Human fibrosarcoma cells | 1.577 | 0.706 |
| Aspc-1 | Human pancreatic cancer cells | 2.475 | 0.689 |

The descriptions above are merely preferred embodiments of the present invention, and it should be noted that those of ordinary skills in the art may make a plurality of improvements and modifications without departing from the principle of the present invention, and these improvements and modifications shall also fall within the protection scope of the present invention.

The invention claimed is:

1. An N-macrocyclic amide compound, or an isomer, a diastereomer, an enantiomer, a prodrug or a pharmaceutically acceptable salt thereof, wherein the isomer is a geometric isomer in the form of an E isomer, a Z isomer, or a mixture of E and Z isomers; and wherein a structure of the N-macrocyclic amide compound is shown in a general structural formula (I) or a general structural formula (II):

General structural formula (I)

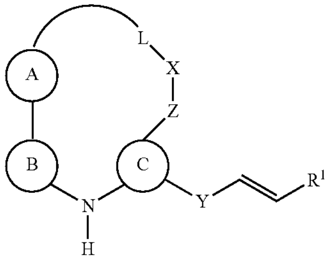

General structure formula (II)

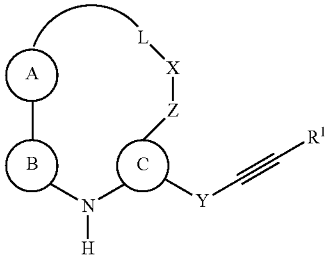

in the general structural formula (I) or the general structural formula (II),

L is a group represented by the following formula:

$-L^1-L^2-$, one end of $L^1$ in the formula is connected to A group, and one end of $L^2$ is connected to X group;

$L^1$ is selected from: a covalent bond, alkyl, —O—, —S—, —N($R^2$)—, alkyl-O—, —O-alkyl, alkyl-O-alkyl, alkyl-S—, —S-alkyl, alkyl-S-alkyl, alkyl-N($R^2$)—, —N($R^2$)-alkyl, or alkyl-N($R^2$)-alkyl;

$L^2$ is selected from: a covalent bond, alkyl, alkyl-CH═CH—, or —CH═CH-alkyl;

X is selected from: a covalent bond, —O—, —S—, or —$NR^2$—;

Y is selected from: —O—, —S—, —N($R^2$)—, —N($R^2$)—CO—, —O-alkyl, —S-alkyl, —N($R^2$)-alkyl, or —N($R^2$)—CO-alkyl;

Z is selected from: a covalent bond or alkyl, wherein one or more carbons in a carbon chain of the alkyl can be substituted by a heteroatom;

$R^1$ group is selected from: H, alkyl, haloalkyl, cycloalkyl, heterocycloalkyl, aryl, heteroaryl, cycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, amino, alkylamino, aminoalkyl, carboxy, alkylcarboxy, acylamino, alkylacylamino, alkylsulfonyl, or alkylacyl, wherein each group can optionally be substituted;

or, $R^1$ group is selected from one of the following groups:

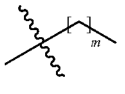
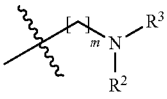
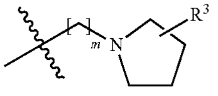

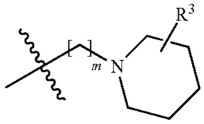
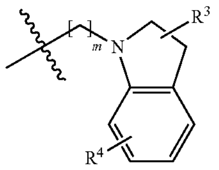

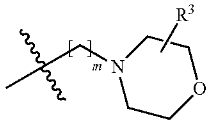
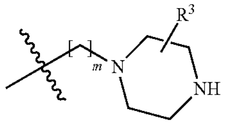

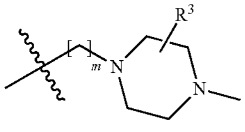
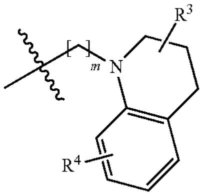

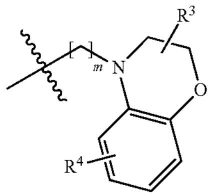
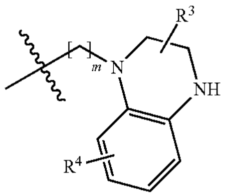

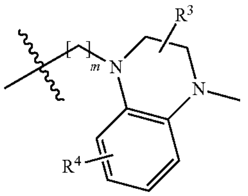
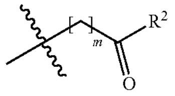

-continued

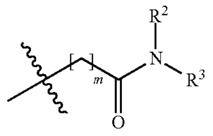

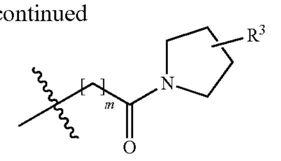

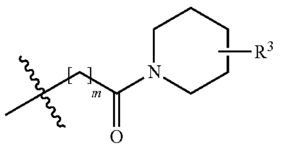

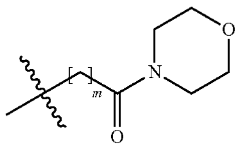

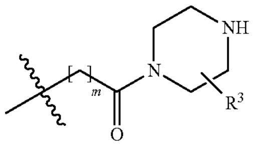

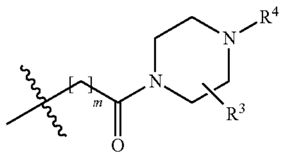

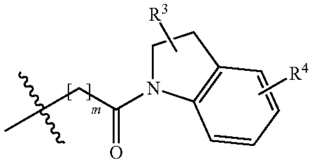

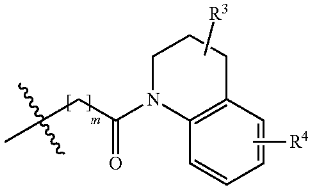

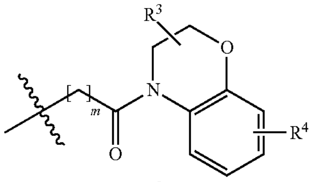

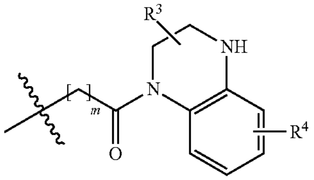

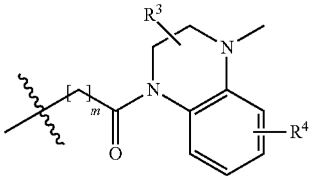

wherein m represents 0 to 3;

$R^2$, $R^3$, and $R^4$ are each independently selected from: H, alkyl, haloalkyl, cycloalkyl, heterocycloalkyl, aryl, heteroaryl, cycloalkyl-alkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, amino, alkylamino, aminoalkyl, carboxy, alkylcarboxy, acylamino, alkylacylamino, alkylsulfonyl, or acyl, wherein each group can optionally be substituted;

A group is selected from:

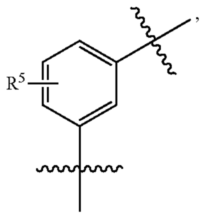

B group is selected from one of the following groups:

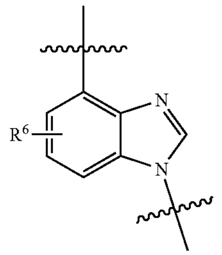

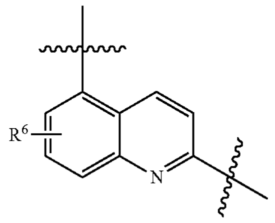

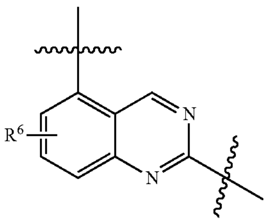

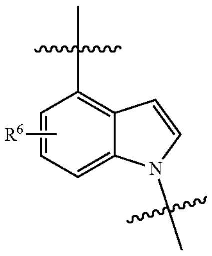

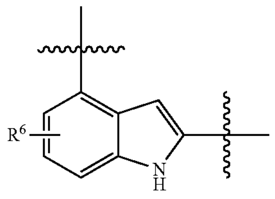

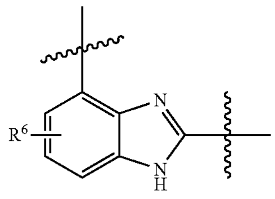

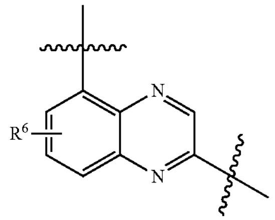

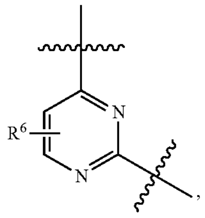

$R^5$ and $R^6$ groups are each independently selected from: H, halogen, alkyl, haloalkyl, heteroalkyl, cycloalkyl, cycloalkenyl, heterocycloalkyl, aryl, heteroaryl, cycloalkylalkyl, arylalkyl, heteroarylalkyl, cycloalkylheteroalkyl, heterocycloalkylheteroalkyl, heteroarylheteroalkyl, arylheteroalkyl, hydroxy, hydroxyalkyl, alkoxy, amino, alkylamino, aminoalkyl, carboxy, alkylcarboxy, acylamino, alkylacylamino, alkylsulfonyl, or acyl, wherein each group can optionally be substituted;

C group is selected from:

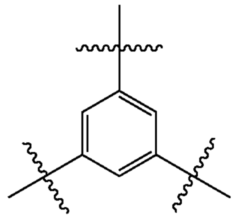

or

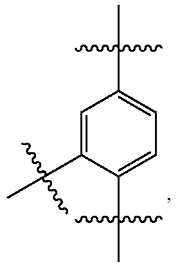

, one of the ends of the formula of C is connected to Y group.

2. The N-macrocyclic amide compound or an isomer, a diastereomer, an enantiomer, a prodrug or a pharmaceutically acceptable salt thereof according to claim 1, wherein:

$L^2$ is selected from: alkyl, alkyl-CH═CH—, or —CH═CH-alkyl;

$R^1$ group is selected from one of the following groups:

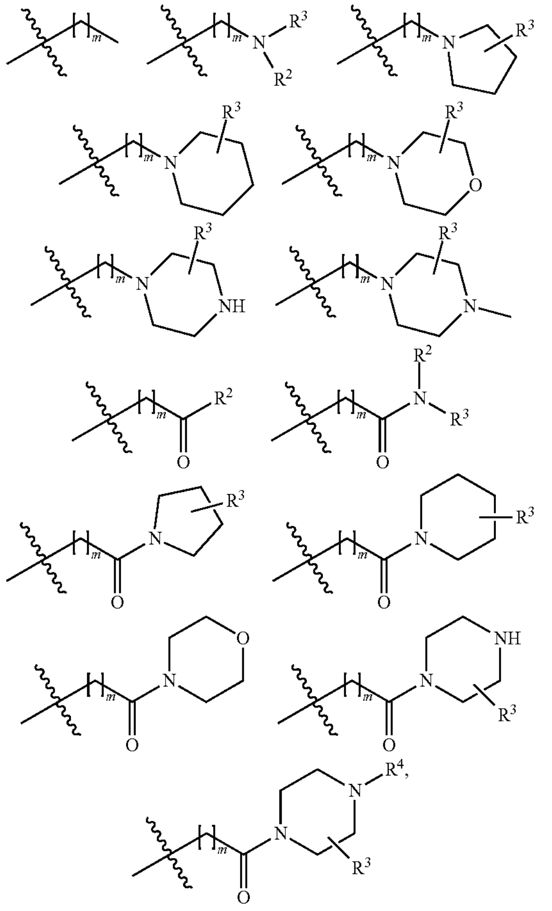

wherein m represents 0 to 3;

X is selected from: —O—, —S—, or —N($R^2$)—;

Y is selected from: —O—, —N($R^2$)—, —O-alkyl, —S-alkyl, —N($R^2$)-alkyl, or —N($R^2$)—CO-alkyl;

B group is selected from:

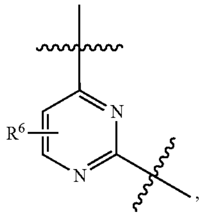

, $R^5$ and $R^6$ groups are each independently selected from: H, halogen, alkyl, haloalkyl, heteroalkyl, cycloalkyl, cycloalkenyl, heterocycloalkyl, aryl, heteroaryl, cycloalkylalkyl, arylalkyl, heteroarylalkyl, cycloalkyl-heteroalkyl, heterocycloalkylheteroalkyl, heteroaryl-heteroalkyl, arylheteroalkyl, hydroxy, hydroxyalkyl, alkoxy, amino, alkylamino, aminoalkyl, carboxy, alkyl-carboxy, acylamino, alkylacylamino, alkylsulfonyl, or acyl, wherein each group can optionally be substituted;

C group is selected from:

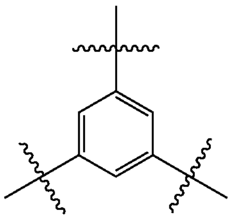

or

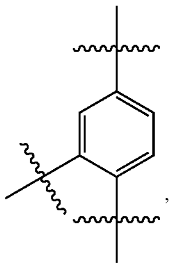

, one of the ends of the formula of C is connected to Y group.

3. The N-macrocyclic amide compound or an isomer, a diastereomer, an enantiomer, a prodrug or a pharmaceutically acceptable salt thereof according to claim 1, wherein:

$L^2$ is selected from: C1-C5 alkyl;

$R^1$group is selected from:

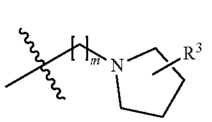

or

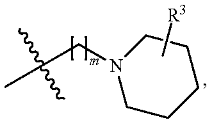

, wherein m represents 0 to 3;

B group is selected from:

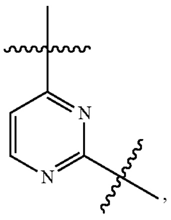 [SMILES: *c1ccnc(*)n1]

,

C group is selected from:

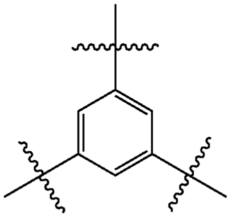

or

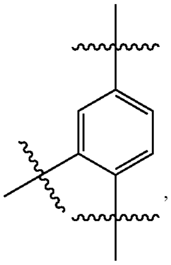

, one of the ends of the formula of C is connected to Y group.

4. The N-macrocyclic amide compound or an isomer, a diastereomer, an enantiomer, a prodrug or a pharmaceutically acceptable salt thereof according to claim 2, wherein:

$L^2$ is selected from: C1-C5 alkyl;

$R^1$group is selected from:

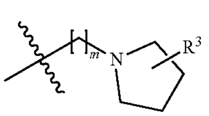

or

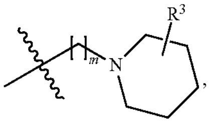

, wherein m represents 0 to 3;

B group is selected from:

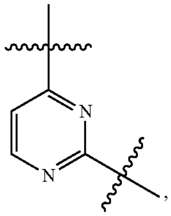 [SMILES: *c1ccnc(*)n1]

,

C group is selected from:

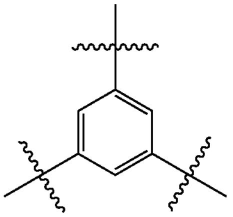

or

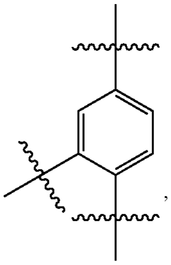

, one of the ends of the formula of C is connected to Y group.

5. An N-macrocyclic amide compound or an isomer, a diastereomer, an enantiomer, a prodrug or a pharmaceutically acceptable salt thereof, wherein the isomer is a geometric isomer in the form of an E isomer, a Z isomer, or a mixture of E and Z isomers; and wherein the compound is one of the following compounds:

XIII-2

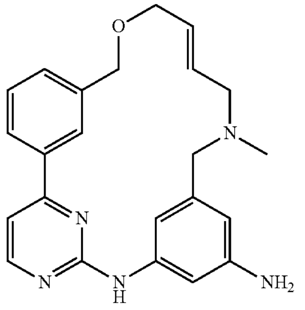

XVI-1

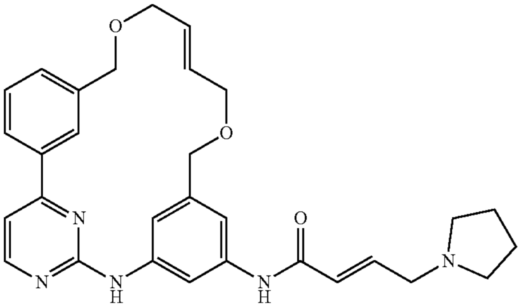

XVI-2

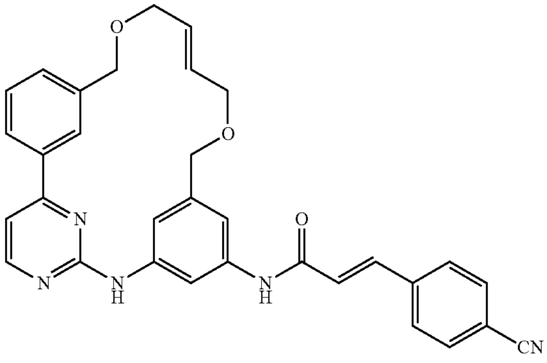

XVI-3

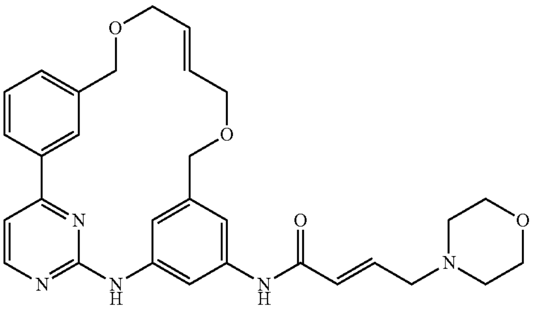

-continued
XVI-4
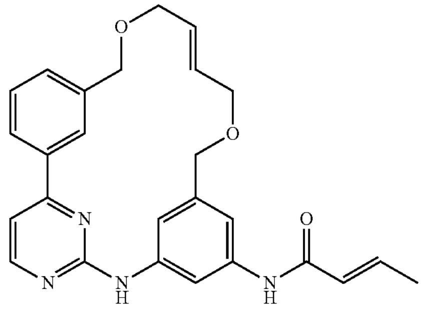
XVI-5
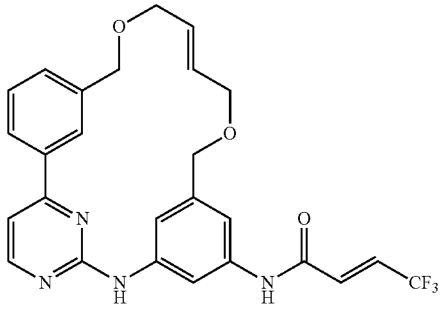
XVI-6
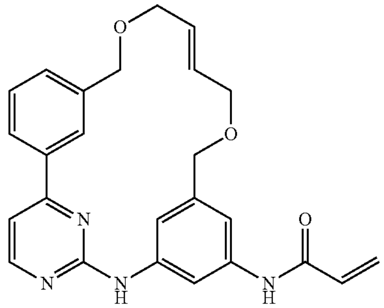
XVI-7
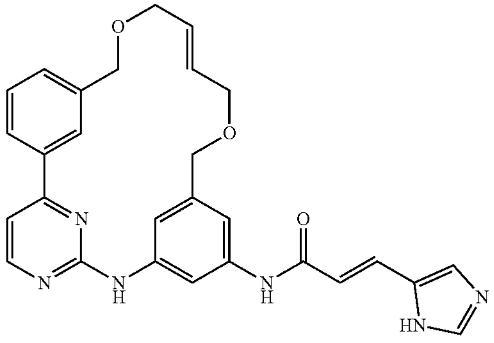
XVI-8
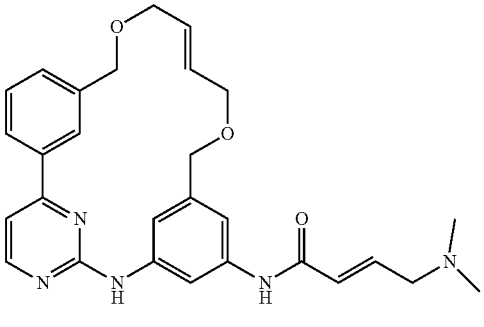
-continued
XVI-9
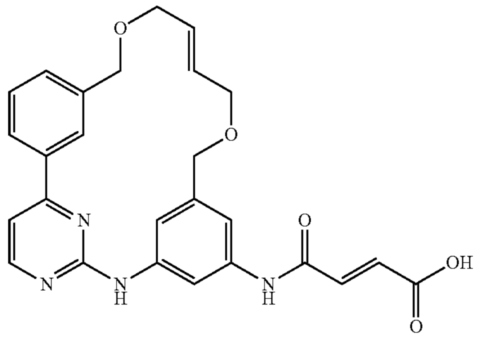
XVI-10
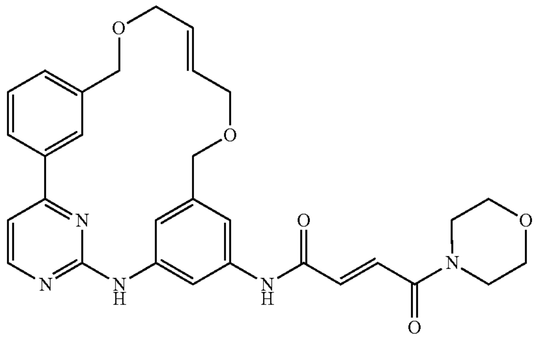
XVI-11
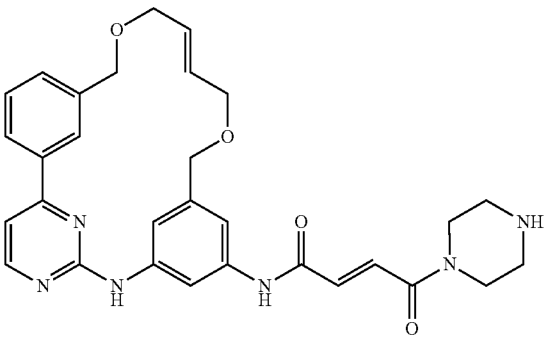
XVI-12
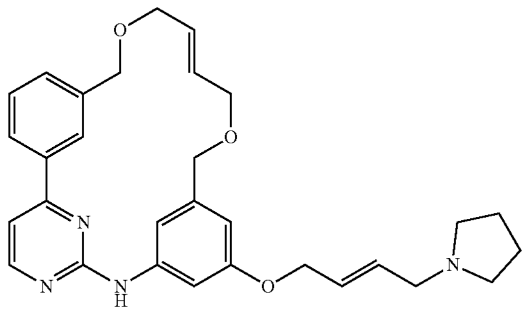

-continued
XVI-13
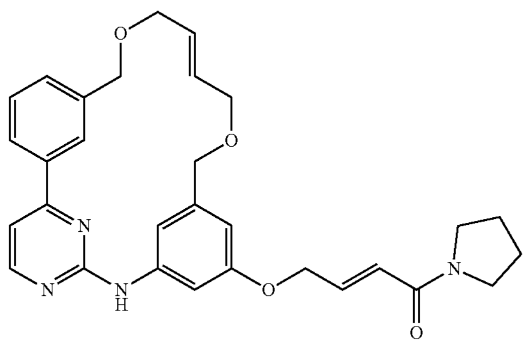
XVI-14
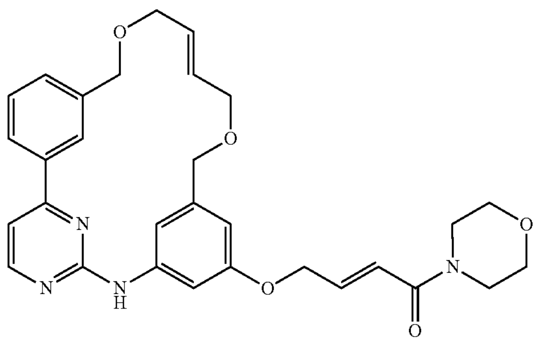
XVI-15
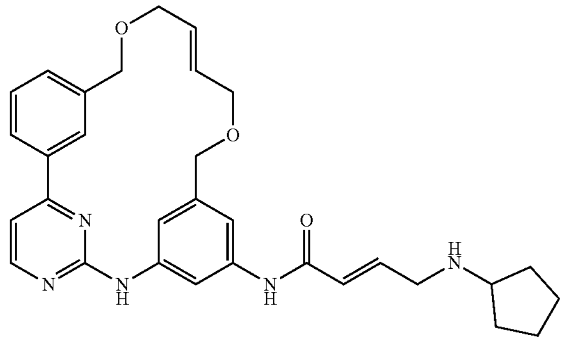
XVI-16
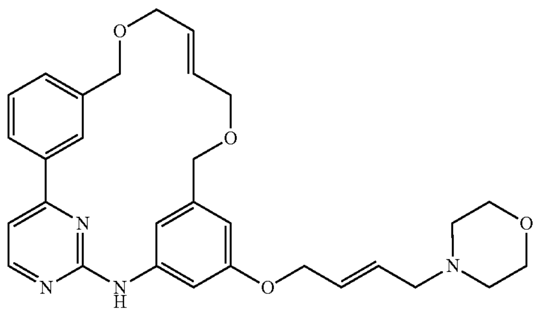
-continued
XVI-17
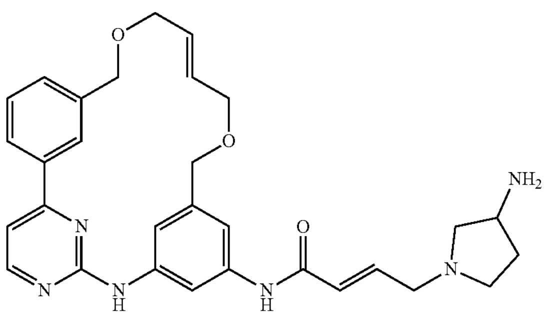
XVI-18
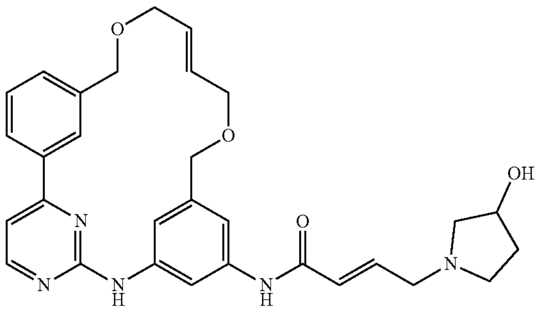
XVI-19
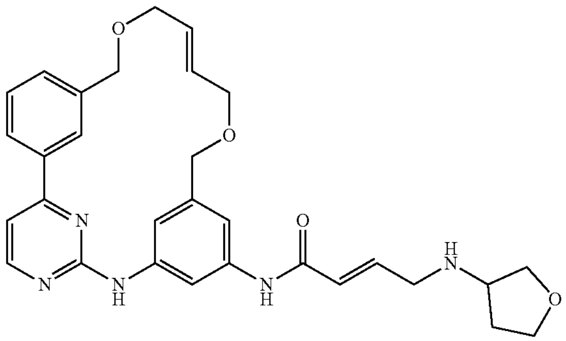
XVI-20
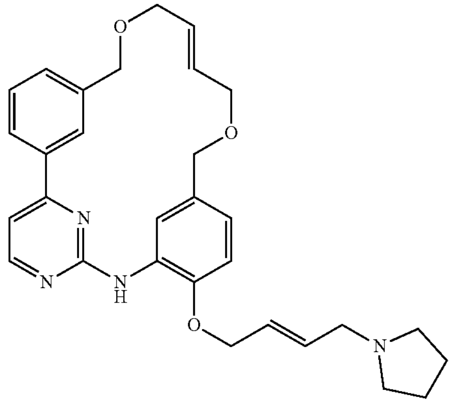

-continued
XVI-21
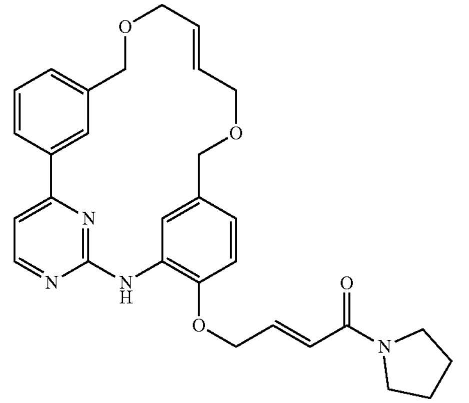
XVI-22
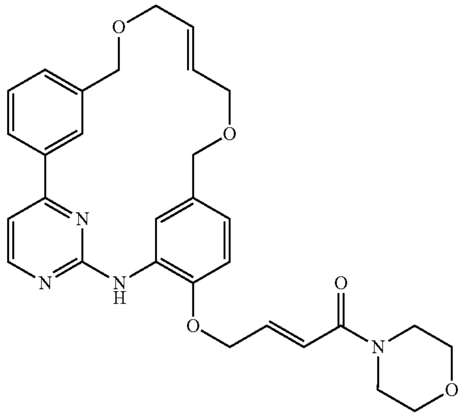
XVI-23
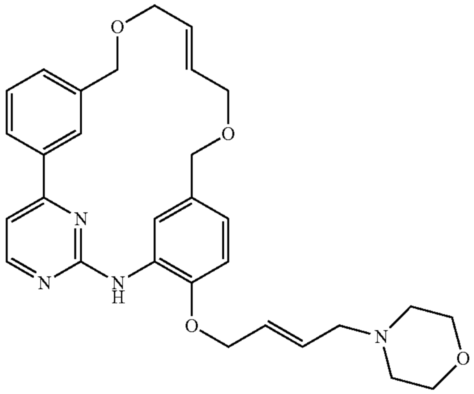
XVI-24
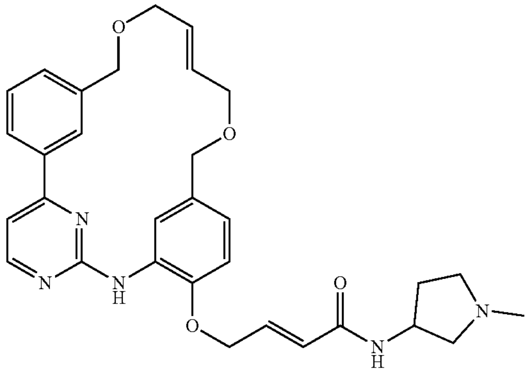
-continued
XVI-25
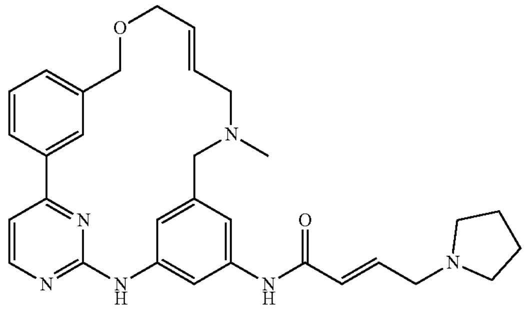
XVI-26
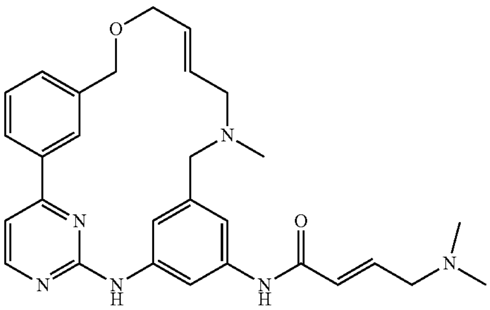
XVI-27
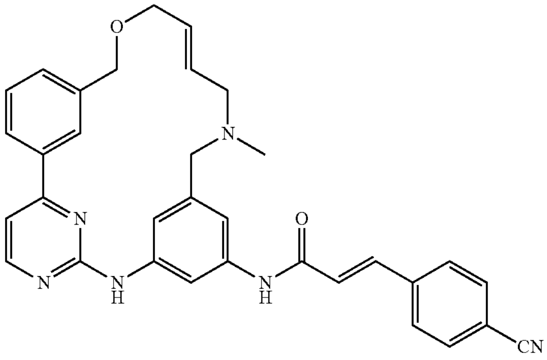
XVI-28
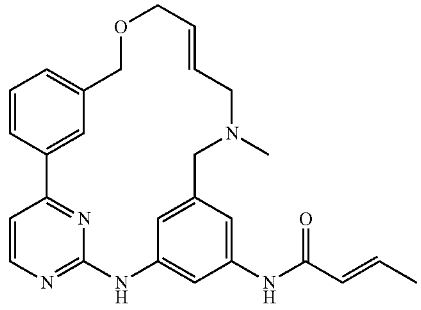

-continued
XVI-29
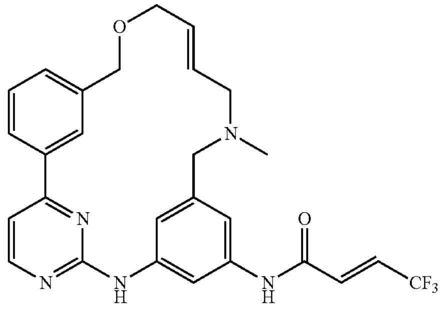
XVI-30
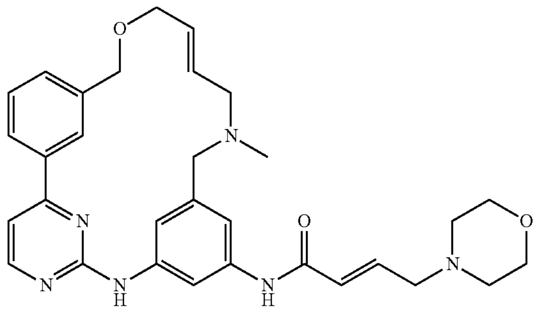
XVI-31
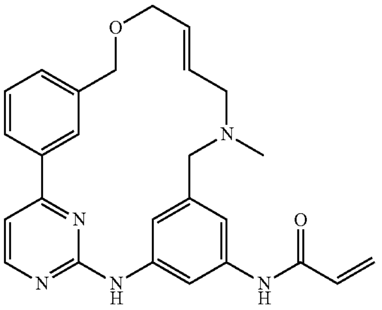
XVI-32
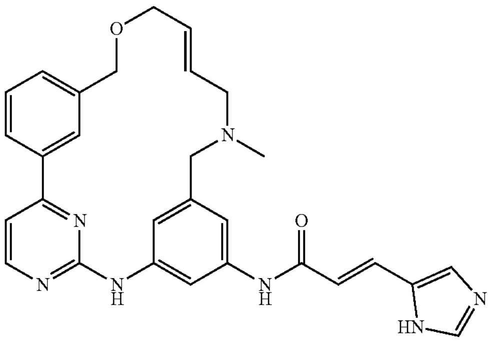
-continued
XVI-33
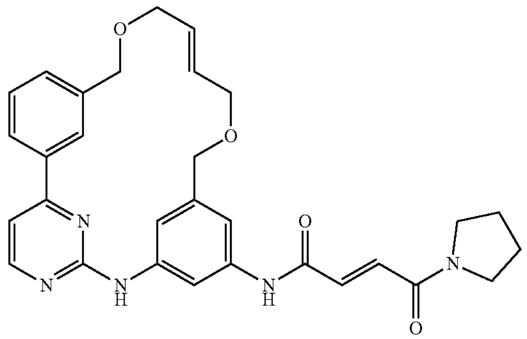
XVI-34
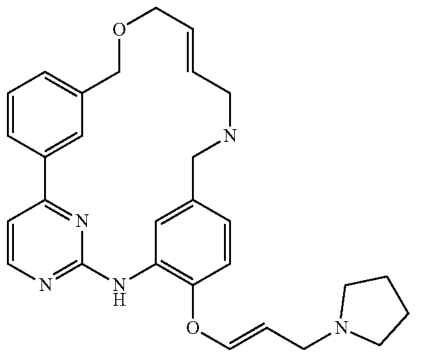
XVII-1
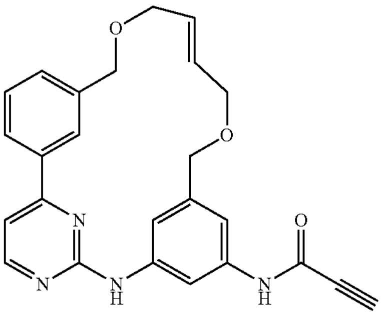
XVII-2
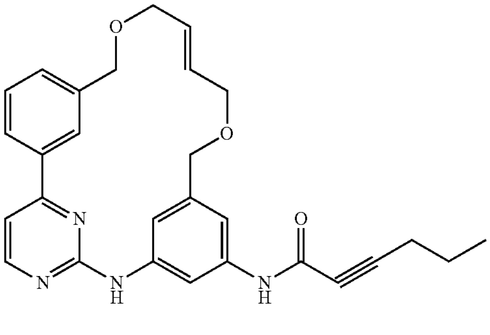

-continued

XVII-3

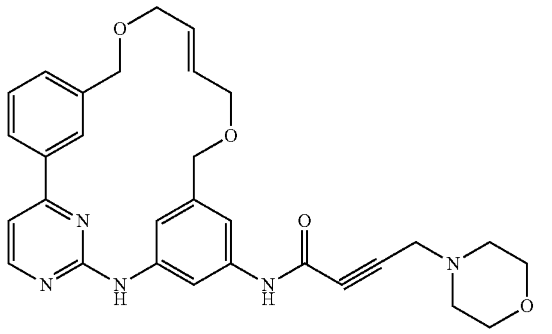

XVII-4

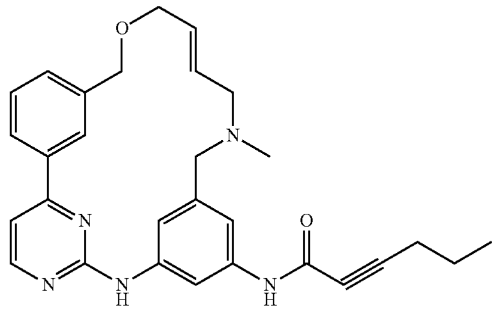

XVII-5

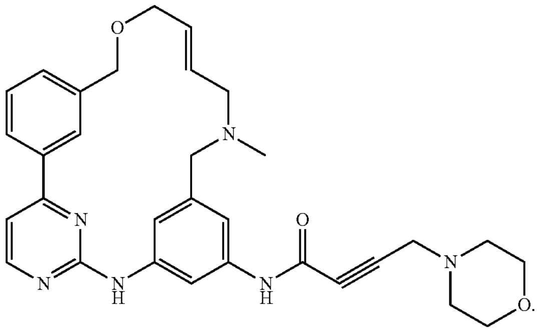

6. A pharmaceutical composition, comprising the N-macrocyclic amide compound or an isomer, a diastereomer, an enantiomer, a prodrug or a pharmaceutically acceptable salt thereof according to claim 1, and one or more of a pharmaceutically acceptable diluent, a pharmaceutically acceptable excipient, and a pharmaceutically acceptable carrier.

7. A method for inhibiting one kinase or a plurality of kinases, comprising administering a therapeutically effective amount of the N-macrocyclic amide compound or an isomer, a diastereomer, an enantiomer, a prodrug or a pharmaceutically acceptable salt thereof according to claim 1, or a pharmaceutical composition comprising a N-macrocyclic amide compound or an isomer, a diastereomer, an enantiomer, a prodrug or a pharmaceutically acceptable salt thereof according to claim 1, optionally in combination with a medicament or a plurality of medicaments, wherein the kinase is selected from the group consisting of CDK2, CDK3, CDK4, CDK5, CDK6, CDK9, PCTAIREK, PCTAIRE2, PCTAIRE3, CAK/MO15, Dm2, Dm2c, Ddcdc2, DdPRK, LmmCRKK, PfC2R, EhC2R, CfCdc2R, cdc2+, CDC28, PHO85, KIN28, FpCdc2, MsCdc2B, OsC2R, PDGFR-b, PDGFR-a, CSFIR, c-kit, Flk2, FLT1, FLT2, FLT3, FLT4, TYK2, JAK1, JAK2, and HOP.

8. A method for treating a proliferative disease, comprising administering a therapeutically effective amount of the N-macrocyclic amide compound, or an isomer, a diastereomer, an enantiomer, a prodrug or a pharmaceutically acceptable salt thereof according to claim 1, or a pharmaceutical composition comprising a N-macrocyclic amide compound, or an isomer, a diastereomer, an enantiomer, a prodrug or a pharmaceutically acceptable salt thereof according to claim 1, wherein the proliferative disease is selected from the group consisting of myeloproliferative diseases, myeloid metaplasia, chronic myelomonocytic leukemia, acute myelogenous leukemia, juvenile myelomonocytic leukemia, acute promyelocytic leukemia, acute lymphoblastic leukemia, acute erythroblastic leukemia, acute B-cell leukemia, leukocytosis, Hodgkin's disease, B-cell lymphoma, acute T-cell leukemia, breast cancer, ovarian cancer, colon cancer, prostate cancer, melanoma, myelodysplastic syndrome, keloid, retinoblastoma, breast malignant tumor, colon malignant tumor, endometrial hyperplasia, osteosarcoma, squamous cell carcinoma, non-small cell lung cancer, hepatocellular carcinoma, pancreatic malignant tumor, myelogenous leukemia, cervical cancer, fibroma, colonic adenocarcinoma, glioma, glioblastoma, oligodendroglioma, lymphoma, restenosis, astrocytoma, bladder tumor, and musculoskeletal tumor.

9. The method according to claim 8, wherein the proliferative disease is selected from the group consisting of prostate cancer, retinoblastoma, breast malignant tumor, colon malignant tumor, endometrial hyperplasia, osteosarcoma, squamous cell carcinoma, non-small cell lung cancer, melanoma, hepatocellular carcinoma, pancreatic malignant tumor, myelogenous leukemia, cervical cancer, fibroma, colonic adenocarcinoma, T-cell leukemia, glioma, glioblastoma, oligodendroglioma, lymphoma, ovarian cancer, restenosis, astrocytoma, bladder tumor, musculoskeletal tumor, and Alzheimer's disease.

10. The method according to claim 8, wherein the proliferative disease is selected from the group consisting of acute myelogenous leukemia, acute promyelocytic leukemia, acute lymphoblastic leukemia, myelodysplastic syndrome, leukocytosis, juvenile myelomonocytic leukemia, acute B-cell leukemia, chronic myelogenous leukemia, acute T-cell leukemia, myeloproliferative disease, and chronic myelomonocytic leukemia.

11. The method according to claim 8, wherein the proliferative disease is selected from the group consisting of chronic idiopathic myelofibrosis, polycythemia vera, essential thrombocythemia and chronic myelogenous leukemia.

* * * * *